(12) United States Patent
Camras et al.

(10) Patent No.: US 7,641,627 B2
(45) Date of Patent: Jan. 5, 2010

(54) METHOD AND APPARATUS FOR REDUCING INTRAOCULAR PRESSURE

(76) Inventors: Carl B. Camras, 10401 N. 108th St., Omaha, NE (US) 68142; Lucinda J. Camras, 10401 N. 108th St., Omaha, NE (US) 68142

( * ) Notice: Subject to any disclaimer, the term of this patent is extended or adjusted under 35 U.S.C. 154(b) by 79 days.

(21) Appl. No.: 11/063,623

(22) Filed: Feb. 23, 2005

(65) Prior Publication Data
US 2006/0189915 A1   Aug. 24, 2006

(51) Int. Cl.
*A61M 5/00*   (2006.01)
(52) U.S. Cl. .................... 604/9; 604/8; 604/264
(58) Field of Classification Search .......... 604/7–10, 604/264, 30, 6.09, 6.1; 606/153, 108
See application file for complete search history.

(56) References Cited

U.S. PATENT DOCUMENTS

| | | | |
|---|---|---|---|
| 4,886,488 A | | 12/1989 | White |
| 5,127,901 A | * | 7/1992 | Odrich ............... 604/9 |
| 5,300,020 A | * | 4/1994 | L'Esperance, Jr. ....... 604/9 |
| 5,346,464 A | * | 9/1994 | Camras ............... 604/9 |
| 5,743,868 A | | 4/1998 | Brown et al. |
| 5,807,302 A | | 9/1998 | Wandel |
| 5,830,173 A | * | 11/1998 | Avery et al. ........... 604/9 |
| 6,537,241 B1 | * | 3/2003 | Odland ............... 604/9 |
| 6,558,342 B1 | * | 5/2003 | Yaron et al. ........... 604/9 |
| 6,595,945 B2 | | 7/2003 | Brown |
| 6,881,198 B2 | * | 4/2005 | Brown ............... 604/8 |
| 7,135,009 B2 | * | 11/2006 | Tu et al. ............. 604/8 |
| 2007/0254005 A1 | * | 11/2007 | Pathak et al. .......... 424/423 |

* cited by examiner

*Primary Examiner*—Leslie R Deak
(74) *Attorney, Agent, or Firm*—Greer, Burns & Crain, Ltd.

(57) ABSTRACT

A drainage apparatus and method to reduce intraocular pressure in an eyeball that includes an anterior chamber having aqueous humor disposed therein, a cornea and a surrounding marginal limbus by which the cornea is continuous with a scleral layer and a conjunctival layer disposed on an exposed surface of the eyeball and under eyelids, the apparatus comprising an inlet assembly configured to be disposed at the anterior chamber of the eyeball, an outlet assembly configured to be disposed at the external surface of the eyeball, a tube extending between the inlet and outlet assemblies and configured to promote fluid communication between the inlet and outlet assemblies, and a control means disposed within the outlet assembly for controlling a flow of aqueous humor through the tube from the anterior chamber of the eyeball to the external surface of the eyeball, and for preventing bacterial infiltration into the anterior chamber.

27 Claims, 19 Drawing Sheets

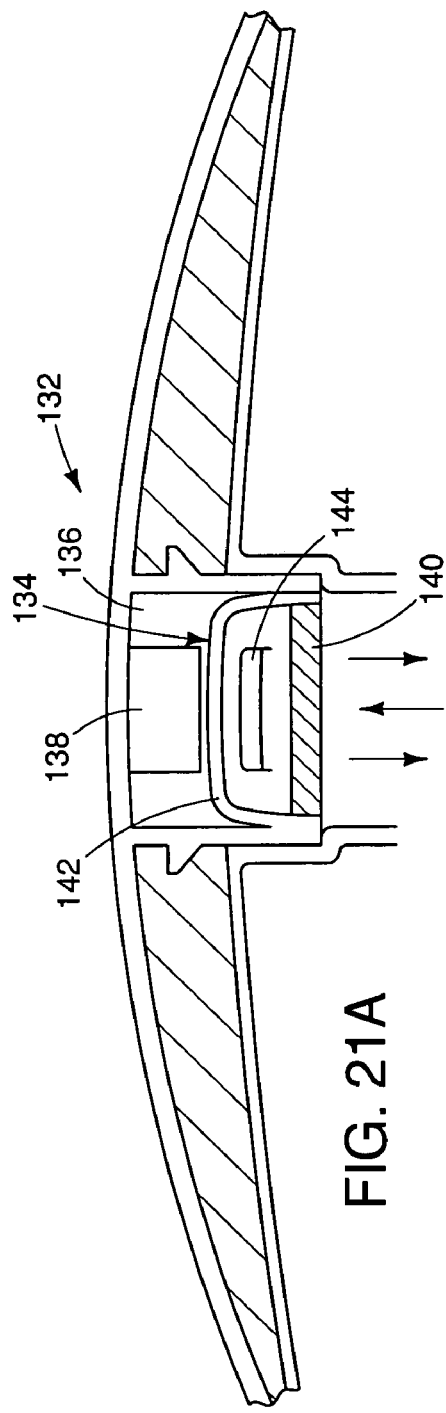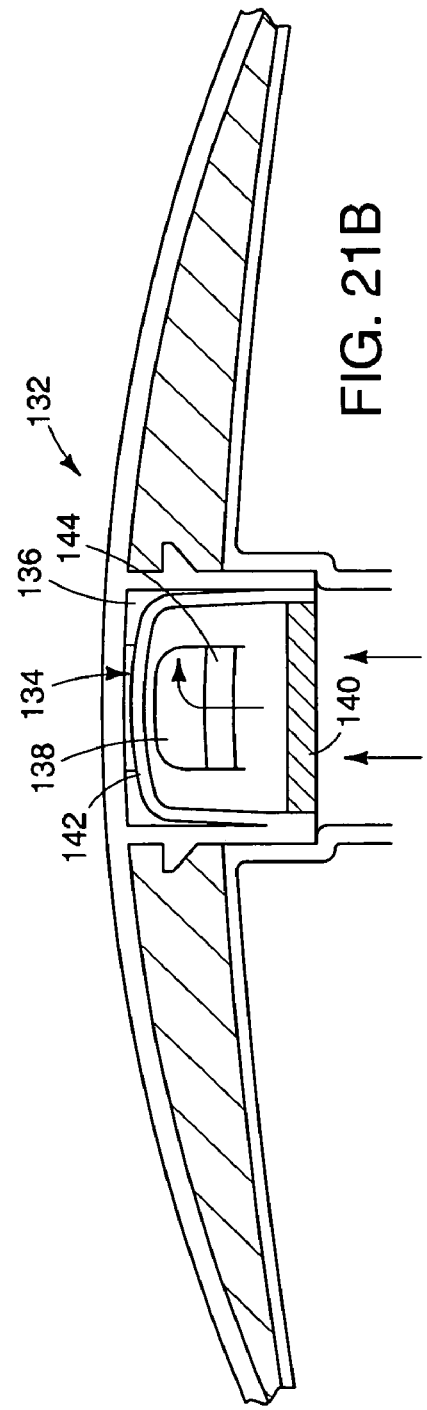

METHOD AND APPARATUS FOR REDUCING INTRAOCULAR PRESSURE

BACKGROUND OF THE INVENTION

The present invention relates to the field of medical technology, particularly to an apparatus to be implanted in an eyeball for the treatment of glaucoma.

Glaucoma is one of the leading causes of blindness in the United States. It is estimated that two to three million people in the United States have some degree of visual loss resulting from glaucoma. While glaucoma is a medical condition which can be caused by several factors, excessive intraocular pressure is a major risk factor for developing glaucoma. Over time, excessive intraocular pressure can cause damage to the optic nerve resulting in gradual loss of vision and, in some cases, blindness. Excessive intraocular pressure is caused by an increase in the resistance to outflow of fluid, called aqueous humor, in the anterior chamber of the eyeball, which can be caused by a number of different factors including injury, the aging process, reaction to medication (such as corticosteroids), structural abnormalities within the eyeball, and a genetic predisposition.

Aqueous humor is a clear, watery fluid which is constantly circulated within the anterior chamber of the eyeball. It serves to nourish the cornea and lens and to provide the intraocular pressure necessary to maintain the shape of the eyeball. Aqueous humor exits the anterior chamber through a network of spongy tissue called the trabecular meshwork, which is located in the intersecting space (the angle) between the iris and the cornea. Increased intraocular pressure results when aqueous humor cannot drain properly or at an appropriate rate through the trabecular meshwork or other outflow pathways. The only proven treatment for glaucoma is to reduce intraocular pressure.

Increased intraocular pressure can in some cases be treated with appropriate medication. These medications are usually administered through pills or eye drops and work to either decrease the rate at which aqueous humor flows into the eyeball, or to increase the rate at which aqueous humor drains from the eyeball. However, as with any medication, patients experience different levels of response to the medication, and the side effects of some medications can become intolerable in certain individuals.

Surgical procedures are also employed to treat glaucoma. Certain procedures are referred to as "filtration" procedures, since the end goal of these particular surgical procedures is to increase the outflow of aqueous humor from the anterior chamber, thereby reducing intraocular pressure. Procedures focused on increasing the outflow of aqueous humor from the anterior chamber of the eyeball are theoretically more beneficial than those designed to decrease the production of aqueous humor, as over 95% of glaucomatous disease is a consequence of increased outflow resistance or reduced outflow rate rather than increased aqueous humor production or increased venous pressure distal to the outflow channels. Full thickness filtration surgical procedures involve the creation of an alternate route for the aqueous humor to flow from the anterior chamber of the eyeball into the subconjuctival space with the formation of a bleb—an area of limbal (anterior) filtration—which contains the aqueous humor. Guarded filtration surgical procedures, such as a trabeculectomy, involve the surgical creation of an opening which is covered by partial thickness sclera, from the anterior chamber into the subconjunctival space, thereby resulting in increased aqueous humor flow out of the anterior chamber. Unfortunately, the failure rate of filtration procedures is unacceptably high. In addition, postoperative intraocular pressure is almost always unstable and unpredictable. Initial overdrainage can lead to abnormally low intraocular pressure, known as hypotony, which can cause the eyeball to malfunction and delay the patient's postoperative recovery. Also, scarring or excessive resistance may occur in the subconjunctival, episcleral, or scleral regions (i.e., the sclerostomy site or surgical opening into the anterior chamber), thereby restricting the drainage.

Surgical procedures have also been used to reduce the amount of aqueous humor production within the eyeball. Ciliodestructive surgery, also known as cyclocryotherapy or cyclophotocoagulation, involves the use of either cryotherapy or a laser on the surface of the eyeball to reduce the production of aqueous humor. However, this procedure can cause a decrease in vision, and is usually used as a last resort when other procedures have failed.

Another method of treating intraocular pressure involves the use of drainage devices implanted within the anterior chamber as a means to drain aqueous humor while maintaining proper intraocular pressure. These devices typically incorporate a tube situated within the anterior chamber which drains aqueous humor from the anterior chamber into a surgically created posterior reservoir, called a fibrous capsule, formed around the scleral explant of the device. The aqueous humor which drains into the fibrous capsule is eventually resorbed by the body. Some of these drainage devices employ valve mechanisms to provide resistance to aqueous humor outflow. These valves have been shown to be unpredictable in their performance, resulting in excessive outflow of aqueous humor and possible hypotony. The valves can also become clogged and cease to function altogether, which results in an increase in intraocular pressure. Also, the fibrous capsule can become scarred or can develop excessive resistance, resulting in failure and a need for surgical revision. In addition, the insertion process for properly implanting these drainage devices within the eyeball can often be very complex and time consuming, increasing the duration of the surgical procedure itself and the postoperative recovery period for the patient.

Certain drainage devices have been developed to reduce intraocular pressure by draining aqueous humor from the anterior chamber to the external surface of the eyeball, as shown by U.S. Pat. No. 5,346,464 to Camras (see also U.S. Pat. Nos. 6,595,945 to Brown, 4,886,488 to White, 5,743,868 to Brown and 5,807,302 to Wandel). These drainage devices have the added benefit of not requiring the creation of a bleb or fibrous capsule for drainage. Therefore, the surgical outcome is not influenced by the possibility of subconjunctival scarring. The devices described in the prior art have not eliminated potential problems such as difficulty of proper insertion, failure of the device, unpredictable postoperative intraocular pressure without a means to compensate or adjust the device for optimal results, and/or extended postoperative recovery time. Additionally, some of these devices do not adequately guard against the potential for infection by entry of microorganisms either through or around the device.

There exists a need in the art for a means to treat glaucoma which is predictable, which allows for the post-surgical adjustment of intraocular pressure, which results in long-term efficacy, which limits the risk of infection, which is comfortable for the patient, and which can be properly inserted both quickly and easily. The present invention meets these needs.

SUMMARY OF THE INVENTION

It is a general object of the present invention to disclose a novel apparatus and method for the treatment of glaucoma.

It is another object of the present invention to provide for a method for using the apparatus to treat glaucoma, involving the insertion of the apparatus into an eyeball and securing the apparatus within and upon the eyeball such that the flow of aqueous humor from the anterior chamber of an eyeball to the external surface of the eyeball is controllable so as to maintain a desirable intraocular pressure.

It is yet another object of the present invention to provide for a tool to insert the apparatus in an eyeball.

It is still another object of the present invention to provide for a method to replace a filter or valve in the apparatus so as to prevent infection and to control the flow of aqueous humor through the apparatus.

Accordingly, the present invention provides for an apparatus to be implanted in an eyeball that includes of a tube having an inlet assembly and an outlet assembly; the outlet assembly being positioned on the external surface of the eyeball; securing means formed upon the inlet assembly, the securing means being capable of securing the inlet assembly within the anterior chamber of the eyeball; and flow control means contained within the outlet assembly to allow the flow of aqueous humor through the apparatus from the anterior chamber of the eyeball to the exterior surface of the eyeball to be controllably regulated to maintain a desired and predictable intraocular pressure.

Additional objects, advantages and novel features of the present invention will be set forth in part in the description which follows, and in part will become apparent to those skilled in the art upon examination of the following, or may be learned from practice of the invention.

DESCRIPTION OF THE DRAWINGS

In the accompanying drawings which form a part of this specification and are to be read in conjunction therewith and in which like reference numerals are used to indicate like parts in the various views:

FIG. 21a is a cross-sectional view of the outlet assembly illustrated in FIGS. 2 and 3 with a valve and filter configured in a relaxed position such that aqueous humor is not exiting to a surface of the eyeball;

FIG. 21b is a cross-sectional view of the outlet assembly illustrated in FIGS. 2 and 3 with a valve and filter configured in a stretched position such that aqueous humor is exiting to a surface of the eyeball;

DESCRIPTION OF THE PREFERRED EMBODIMENTS

Figure 1:
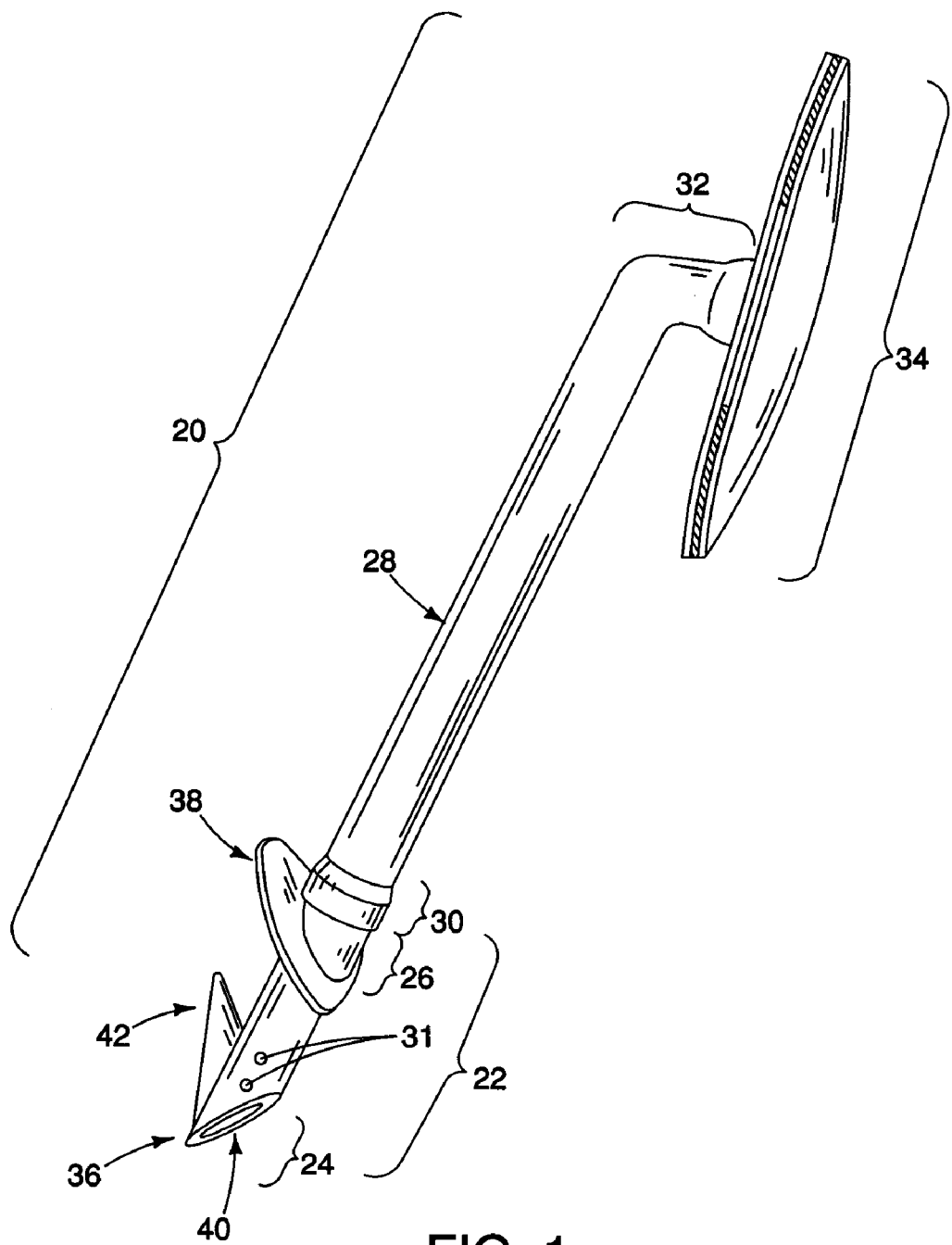
FIG. 1 is a perspective view of a preferred embodiment of a drainage apparatus according to the present invention.

Embodiments of the present invention provide a method and apparatus to direct aqueous humor from the anterior chamber of an eyeball to the external surface of the eyeball as a means to predictably regulate intraocular pressure and treat glaucoma. An embodiment of a drainage apparatus 20 according to the present invention is illustrated in FIG. 1. As shown in FIG. 1, the drainage apparatus 20 includes an inlet assembly 22 having a first end 24 and a second end 26, a tube 28 capable of conducting aqueous humor having a first end 30 and a second end 32, and an outlet assembly 34.

The inlet assembly 22 further includes a beveled tip 36 formed at the first end 24 of the inlet assembly 22, and an insertion plate 38 formed near the second end 26 of the inlet assembly 22. An opening 40 is formed through the inlet assembly 22 allowing aqueous humor to flow through an inner lumen of the inlet assembly 22. An anchor 42 may also be formed near the first end 24 of the inlet assembly 22.

The second end 26 of the inlet assembly 22 is connected to the first end 30 of the tube 28. The tube 28 is capable of conducting aqueous humor through its inner lumen. The second end 32 of the tube 28 is connected to the outlet assembly 34.

Figure 2:
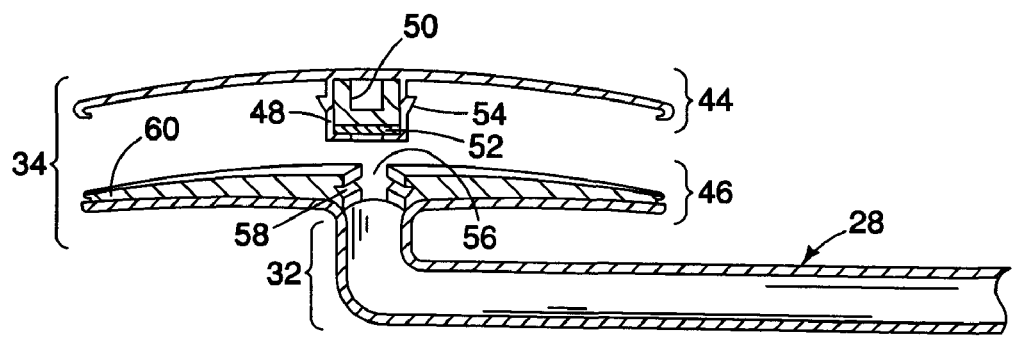
FIG. 2 is a perspective view, partially in cross-section, of the outlet assembly of the preferred embodiment of the drainage apparatus and filter with the outer member separated.
Figure 3:
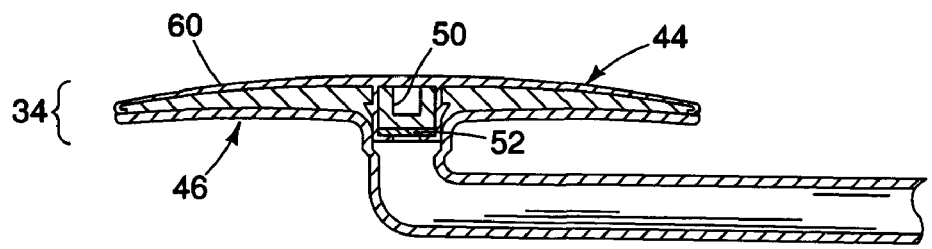
FIG. 3 is another cross-sectional view of the outlet assembly of the drainage apparatus and filter with the outer member attached to the inner member.

As shown in FIGS. 2 and 3, the outlet assembly 34 includes an outer member 44 and an inner member 46. The outer member 44 further includes a central chamber 48 having at least one aperture 50, a filter 52 and a flange 54 disposed along the outer aspect of the central chamber. The inner member 46 includes a central cavity 56, a groove 58 formed therein, and a plurality of spacers 60.

Figure 5:
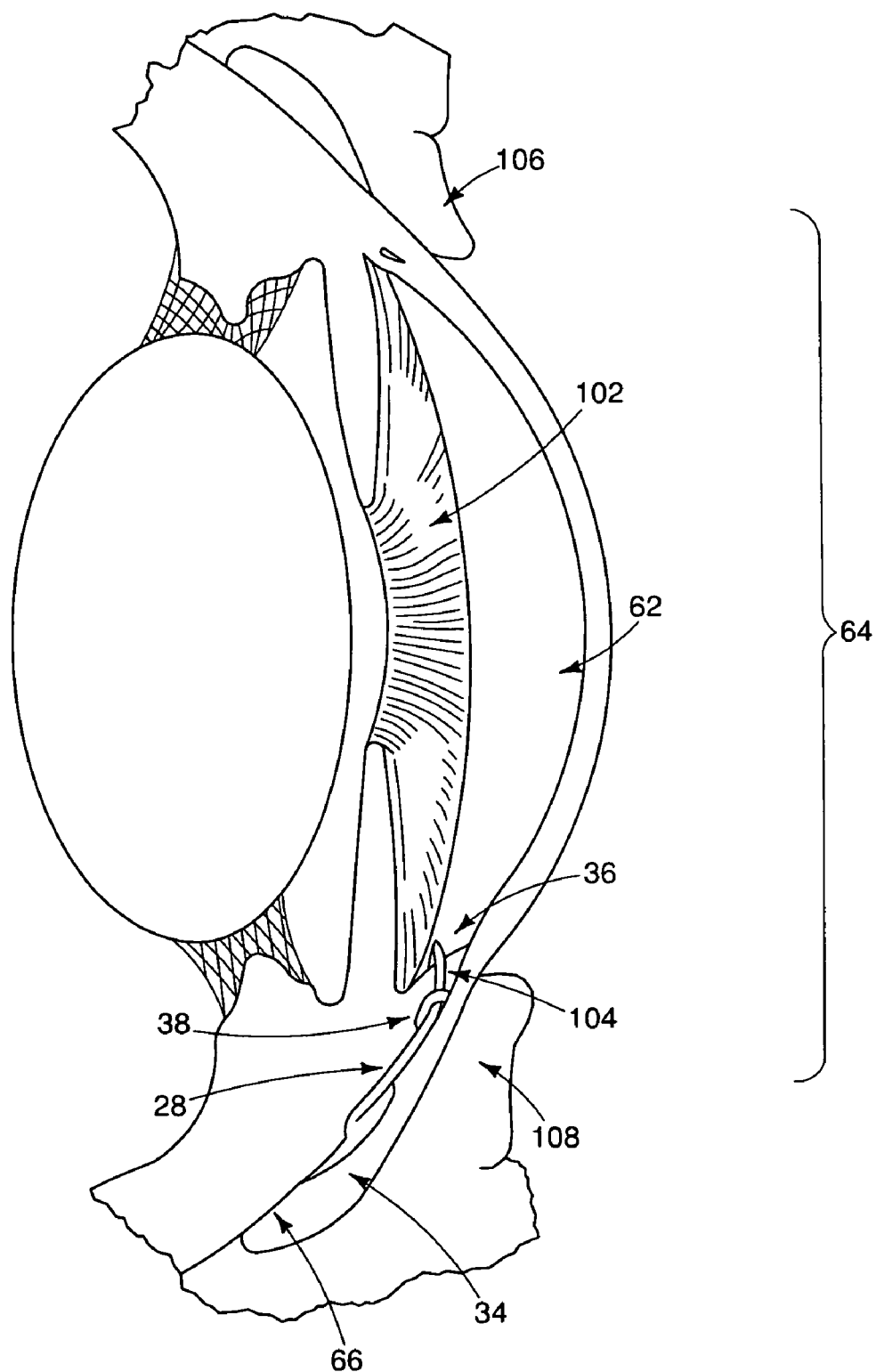
FIG. 5 is a cross-sectional view of an eyeball showing the drainage apparatus inserted therein.
Figure 17:
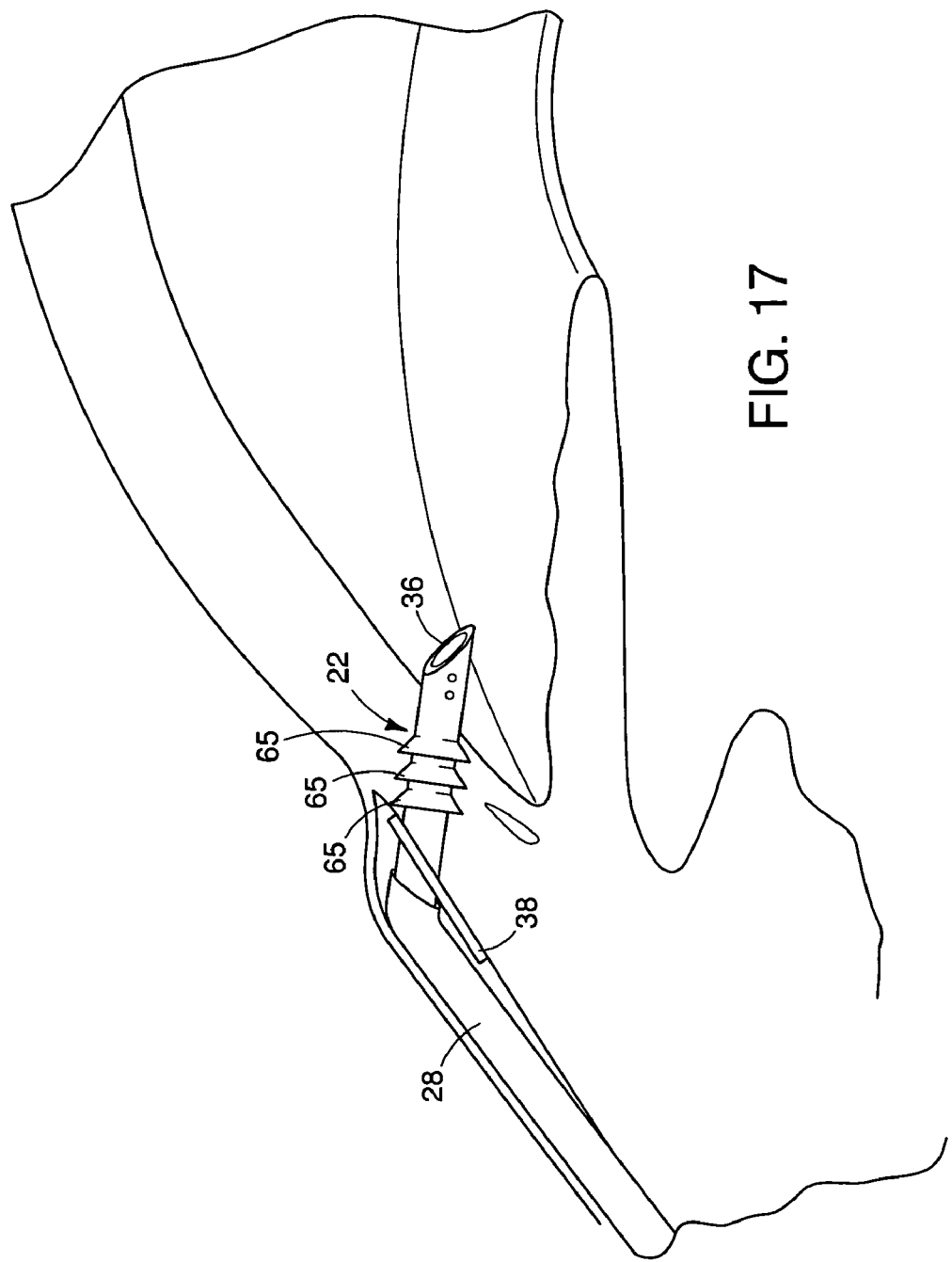
FIG. 17 is a cross-sectional view of an alternative preferred embodiment of the drainage apparatus at a point of insertion into a limbus.
Figure 18:
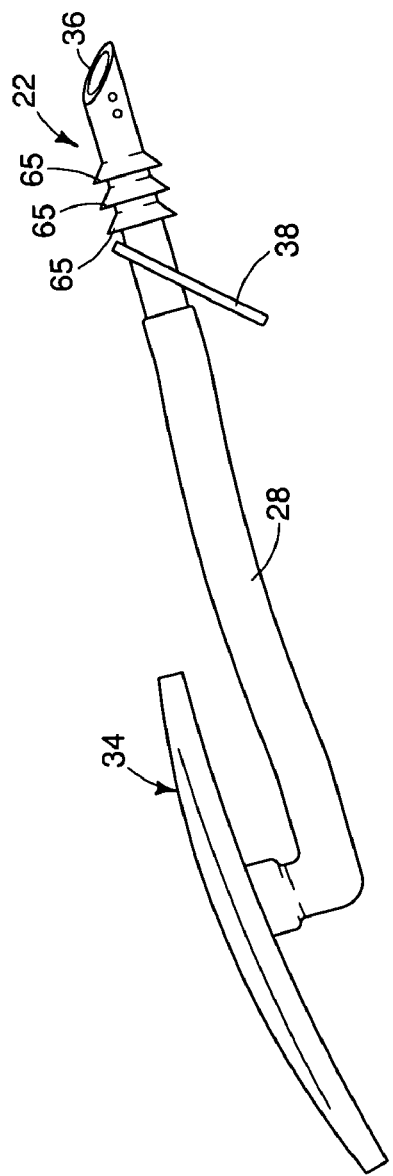
FIG. 18 is a side perspective view of the alternative preferred embodiment of the drainage apparatus illustrated in FIG. 17.
Figure 19:
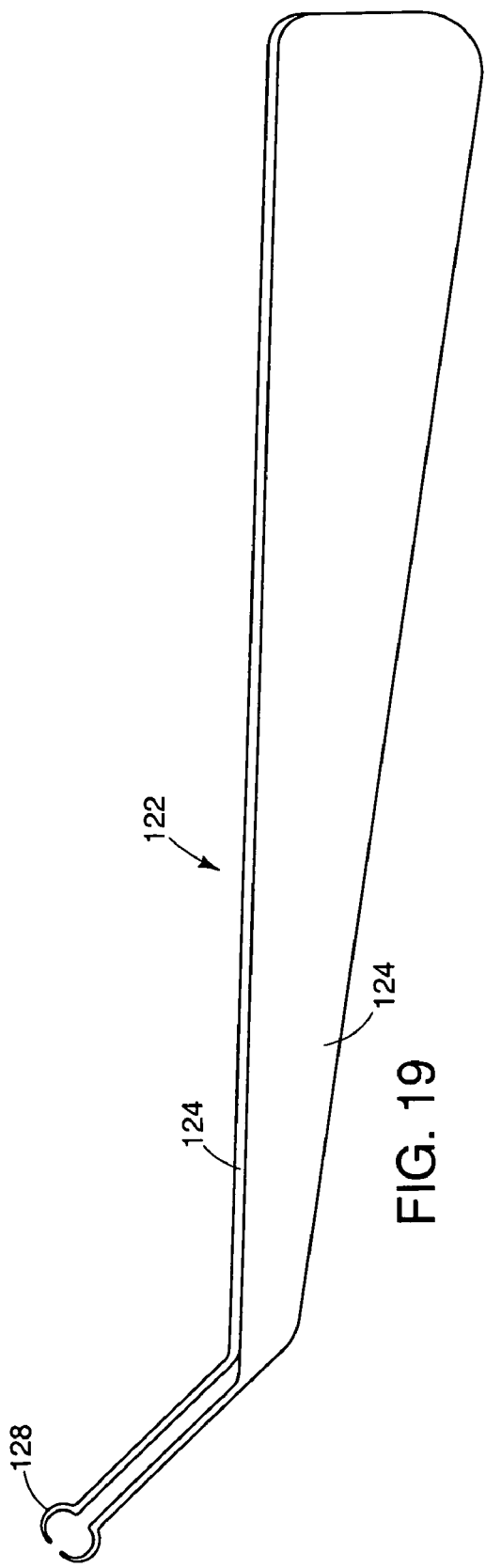
FIG. 19 is a side perspective view of an alternative preferred embodiment of a grasping apparatus for use with one or more preferred embodiments of the drainage apparatus illustrated in FIGS. 1 and 17.
Figure 20:
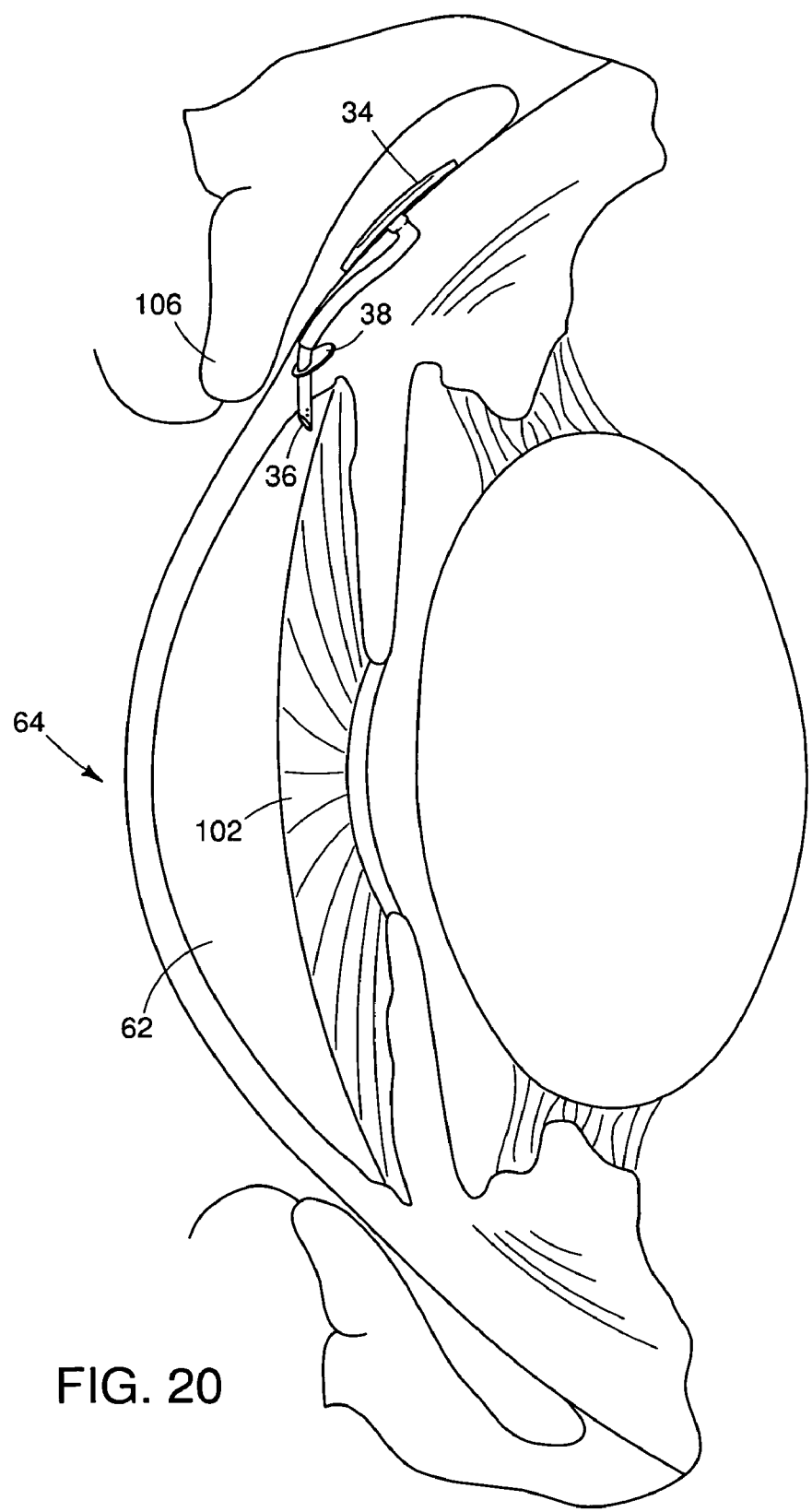
FIG. 20 is a cross-sectional view of an eyeball having the drainage apparatus illustrated in FIGS. 16 and 17 coupled thereto.

As shown in FIGS. 1 and 5, the shape of the beveled tip 36 of the inlet assembly 22 allows the first end 24 and opening 40 of the inlet assembly 22 to be more easily inserted into the anterior chamber 62 of an eyeball 64 during the process of inserting the drainage apparatus 20 into the eyeball described in detail below. An anchor 42 may be disposed on the outer aspect near the first end 24 of the inlet assembly 22. In this position, the anchor 42 will help to secure the beveled tip 36 of the first end 24 of the inlet assembly 22 within the anterior chamber 62 of the eyeball 64. Alternatively, as illustrated in FIGS. 17, 18 and 20, a plurality of anchors 65 may be formed on the outer aspect of the first end 24 of the inlet assembly 22, thereby allowing the first end of the inlet assembly 22 to be secured at a number of different lengths within the anterior chamber 62 as may be necessary in certain afflicted eyeballs.

In the preferred embodiment shown in FIGS. 1-4, inlet assembly 22 and tube 28 are formed as one unit. In other embodiments, inlet assembly 22 and tube 28 may be formed separately from the same or different materials. When formed separately, the second end 26 of the inlet assembly 22 is attached to the first end 30 of the tube 28. The tube 28 may be formed such that the inner diameter of the first end 30 of the tube is slightly smaller than the outer diameter of the second end 26 of the inlet assembly 22. This allows the second end 26 of the inlet assembly 22 to be inserted into the first end 30 of the tube 28, so that the second end 26 of the inlet assembly and the first end of the tube are held together by a frictional fit. Other known methods of attaching the first end 30 of the tube 28 to the second end 26 of the inlet assembly 22 may also be employed for this purpose.

As shown in FIGS. 2, 3 and 5, both the outer member 44 and inner member 46 of the outlet assembly 34 are preferably round and convex in shape, similar to a contact lens, thereby allowing the outlet assembly of the drainage apparatus 20 to sit comfortably on the external surface of the conjunctival layer 66 of the eyeball 64 after insertion. While this particular shape is preferable because it helps provide comfort to the patient, other shapes for both the outer member 44 and inner member 46 may also be used with the drainage apparatus 20.

The second end 32 of the tube 28 is connected to the inner member 46 of the outlet assembly 34. The tube 28 and the inner member 46 may be formed as a single unit and may be composed of the same material. Alternatively, the tube 28 and the inner member 46 may be formed separately and secured to each other by a frictional fit as described above or through other methods suitable for this purpose.

Figure 4:
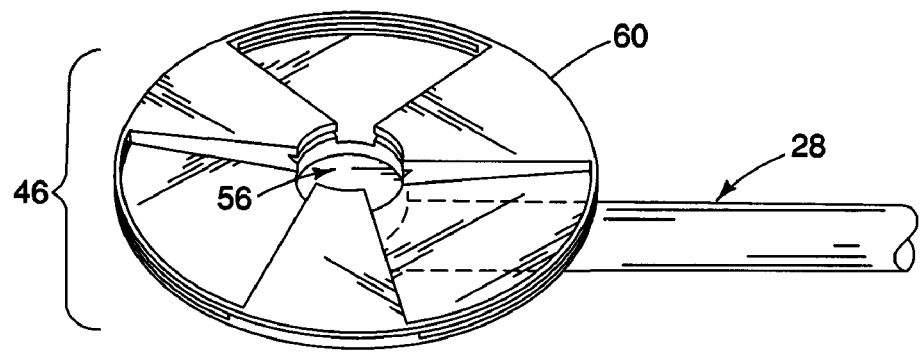
FIG. 4 is a perspective view of the inner member of the outlet assembly of the preferred embodiment of the drainage apparatus.

As shown in FIGS. 2, 3 and 4, a central cavity 56 is formed in the center of the inner member 46. The central chamber 48 of the outer member 44 is received within the central cavity 56. The groove 58 formed within the central cavity 56 serves to receive the flange 54 disposed along the outer aspect of the central chamber 48, thereby securing the central chamber within the central cavity. This also serves to secure the outer member 44 to the inner member 46. As shown in FIG. 3, the central chamber 48 may also extend slightly into the tube 28, further helping to secure the outer member 44 to the inner member 46 by a frictional fit between the tube 28 and the central chamber 48. A gap between the outer member 44 and inner member 46 is maintained by the plurality of spacers 60 formed in the inner member 46. FIG. 4 illustrates one embodiment of the spacers 60 within the inner member 46.

The central chamber 48 of the outer member 44 contains a micropore filter 52. As shown in FIG. 3, when the outer member 44 is secured to the inner member 46, the filter 52 is positioned adjacent to the second end 32 of the tube 28. Aqueous humor flowing from the tube 28 into the outlet assembly 34 is thereby directed through the filter 52. The filter provides resistance to the flow of aqueous humor from the tube 28 into the outlet assembly 34. A filter of greater density (having a smaller pore diameter) will result in increased flow resistance, thereby decreasing the flow of aqueous humor through the drainage apparatus 20 and providing for a higher intraocular pressure. A filter of lesser density (having a larger pore diameter) will result in decreased flow resistance, thereby increasing the flow of aqueous humor through the drainage apparatus 20 and providing for a lower intraocular pressure. In addition, the filter 52 serves as a barrier to microbial infection.

After passing through the filter, the aqueous humor flows out of the central chamber 48 though the apertures 50. The aqueous humor then flows between the spacers 60 into the gap between the outer member 44 and inner member 46. The aqueous humor then drains out of the outlet assembly 34 onto the external surface of the conjunctival layer 66 of the eyeball 64.

Figure 11:
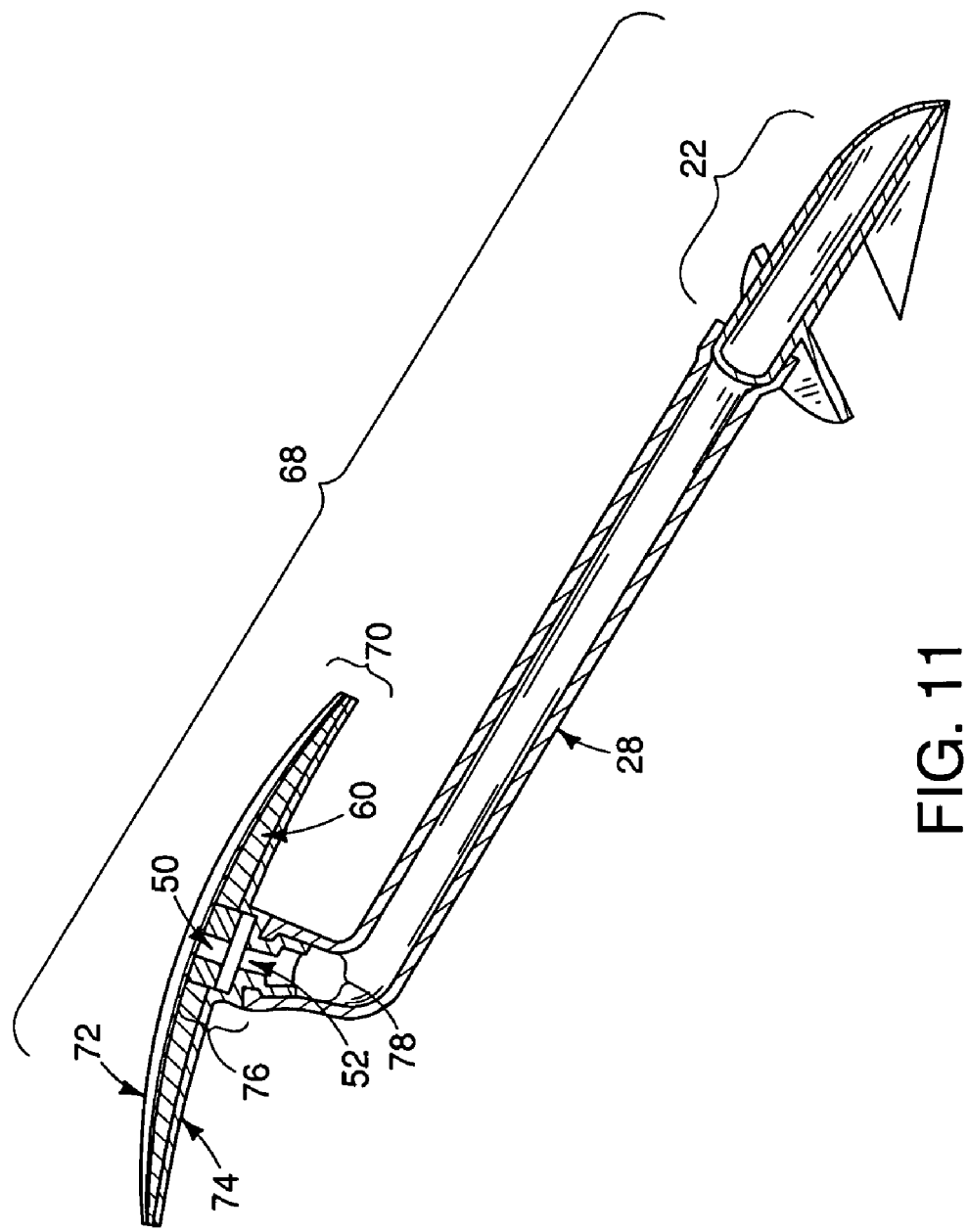
FIG. 11 is a cross-sectional view of another embodiment of the drainage apparatus.

Another embodiment of the present invention is illustrated in FIG. 11 and provides for a drainage apparatus 68 incorporating a one-piece outlet assembly 70. The one-piece outlet assembly 70 includes a first member 72 and a second member 74 which are affixed to each other by means of a chamber 76 and spacers 60. The chamber 76 houses a filter 52 and also contains apertures 50 through which aqueous humor can flow to exit the chamber. A plurality of spacers 60 are disposed between the first member 72 and the second member 74, and serve to maintain a gap between the two so as to allow aqueous humor to flow out of the one-piece outlet assembly 70 onto the external surface of the conjunctival layer 66 of the eyeball 64. Both the first member 72 and second member 74 are optimally round and convex in shape, similar to a contact lens, so as to comfortably fit the external curvature of the eyeball 64. While this shape is beneficial and helps provide comfort to the patient, other shapes for both the first member 72 and second member 74 may also be used with the one-piece outlet assembly 70.

A coupling mechanism 78 is formed on the second member 74 and serves to attach the second end 32 of the tube 28 to the one-piece outlet assembly 70. The coupling mechanism 78 is received within the second end 32 of the tube 28 and is held therein by a frictional fit. The coupling mechanism is hollow, thereby allowing aqueous humor to flow through its inner lumen. The filter 52 is disposed between the coupling mechanism 78 and the apertures 50 within the central chamber 76. The filter provides resistance to the flow of aqueous humor from the tube 28 into the one-piece outlet assembly 70 as described above.

Aqueous humor flows from the tube 28 through the coupling mechanism 78 and is directed through the filter 52. After passing through the filter 52, the aqueous humor flows through the apertures 50 of the chamber 76, into the area between the spacers 60. The aqueous humor then exits the one-piece outlet assembly 70 by flowing through the gap between the first member 72 and second member 74, thereby draining onto the external surface of the conjunctival layer 66 of the eyeball 64.

Figure 6:
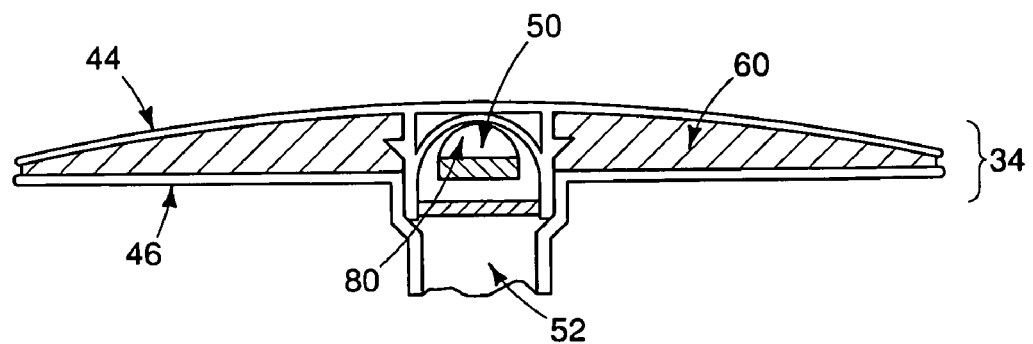
FIG. 6 is a cross-sectional view of the outlet assembly of the drainage apparatus shown in FIGS. 1-4 and valve.

As illustrated in FIG. 6, a valve 80 may also be employed to provide resistance to the flow of aqueous humor through drainage apparatus 20 or 68. When a valve 80 is employed in drainage apparatus 20 or 68, a filter 52 is still required to prevent the ingress of microorganisms, but the filter itself does not provide sufficient resistance to the outflow of aqueous humor from the eyeball 64 to influence the intraocular pressure. The valve 80 is ideally pressure sensitive and unidirectional, and may include a thin membrane of silicone or similar material. The valve 80 is positioned between the filter 52 and the apertures 50 within either the central chamber 48 of the outlet assembly 34 or the chamber 76 of the one-piece outlet assembly 70. In this position, aqueous humor initially flows through the filter 52 before reaching the valve 80. Alternatively, the relative positions of the filter 52 and valve 80 can be reversed so that aqueous humor initially flows through the valve. A sufficient amount of aqueous humor pressure (determined by the intraocular pressure) exerted on valve 80 will cause valve 80 to deform, allowing aqueous humor to flow into the outlet assembly 34 or one-piece outlet assembly 70 and on to the surface of the eyeball 64. Valves of different levels of intraocular pressure resistance may be utilized within drainage apparatus 20 or 68 depending on the desired postoperative level of intraocular pressure within the eyeball 64.

Drainage apparatus 20 and 68 function to drain aqueous humor from the anterior chamber of the eyeball 64 to the external surface of the eyeball. Drainage apparatus 20 or 68 is inserted in the eyeball 64 such that the first end 24 of the inlet assembly 22 is held within the anterior chamber 62 of the eyeball, the tube 28 lies subconjunctivally, conforming to the external curvature of the eyeball, and the outlet assembly 34 or one-piece outlet assembly 70 is positioned above the external surface of the eyeball. Aqueous humor from the anterior chamber 62 of the eyeball 64 enters the opening 40 of the first end 24 of the inlet assembly 22. The aqueous humor flows through the inlet assembly 22 and into the tube 28. The tube 28 conducts the aqueous humor into the outlet assembly 34 or one-piece outlet assembly 70. As the aqueous humor flows into the outlet assembly 34 or one-piece outlet assembly 70, the aqueous humor passes through a filter 52 and perhaps also through a valve 80. The filter functions to provide resistance to the flow of aqueous humor when used alone. If coupled with a valve, the valve instead provides this resistance by having an opening and closing pressure. After flowing through the filter 52 with or without valve 80, the aqueous humor flows through the outlet assembly 34 or one-piece outlet assembly 70 and drains onto the exterior surface of the eyeball 64.

Figure 8:
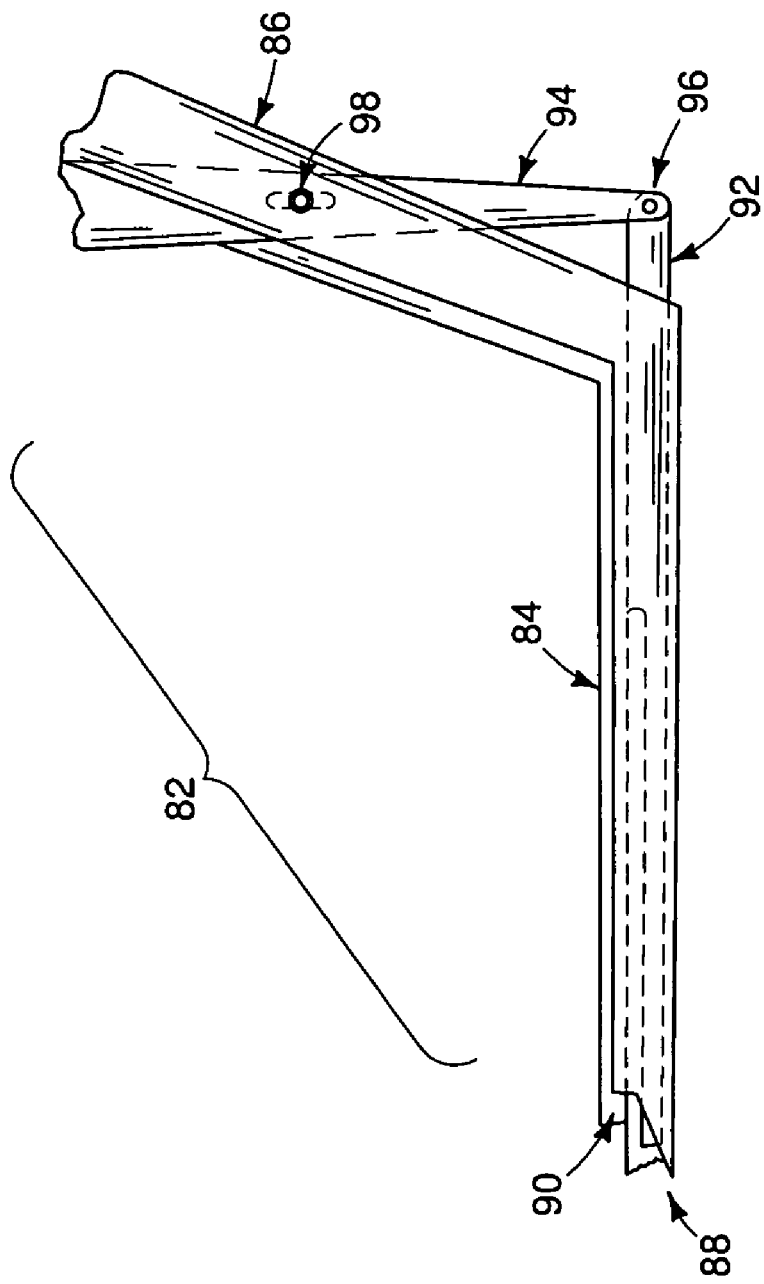
FIG. 8 is a perspective view of a device to insert a drainage apparatus into an eyeball.

The present invention also discloses an apparatus and method for inserting drainage apparatus 20 or 68 into the eyeball 64. FIG. 8 illustrates an inserting apparatus 82 which can be used to insert either embodiment of drainage apparatus 20 or 68 into the eyeball 64. The inserting apparatus 82 is designed to greatly simplify insertion of drainage apparatus 20 or 68 into the eyeball 64 so as to minimize the duration and invasiveness of the insertion procedure.

Figure 9:
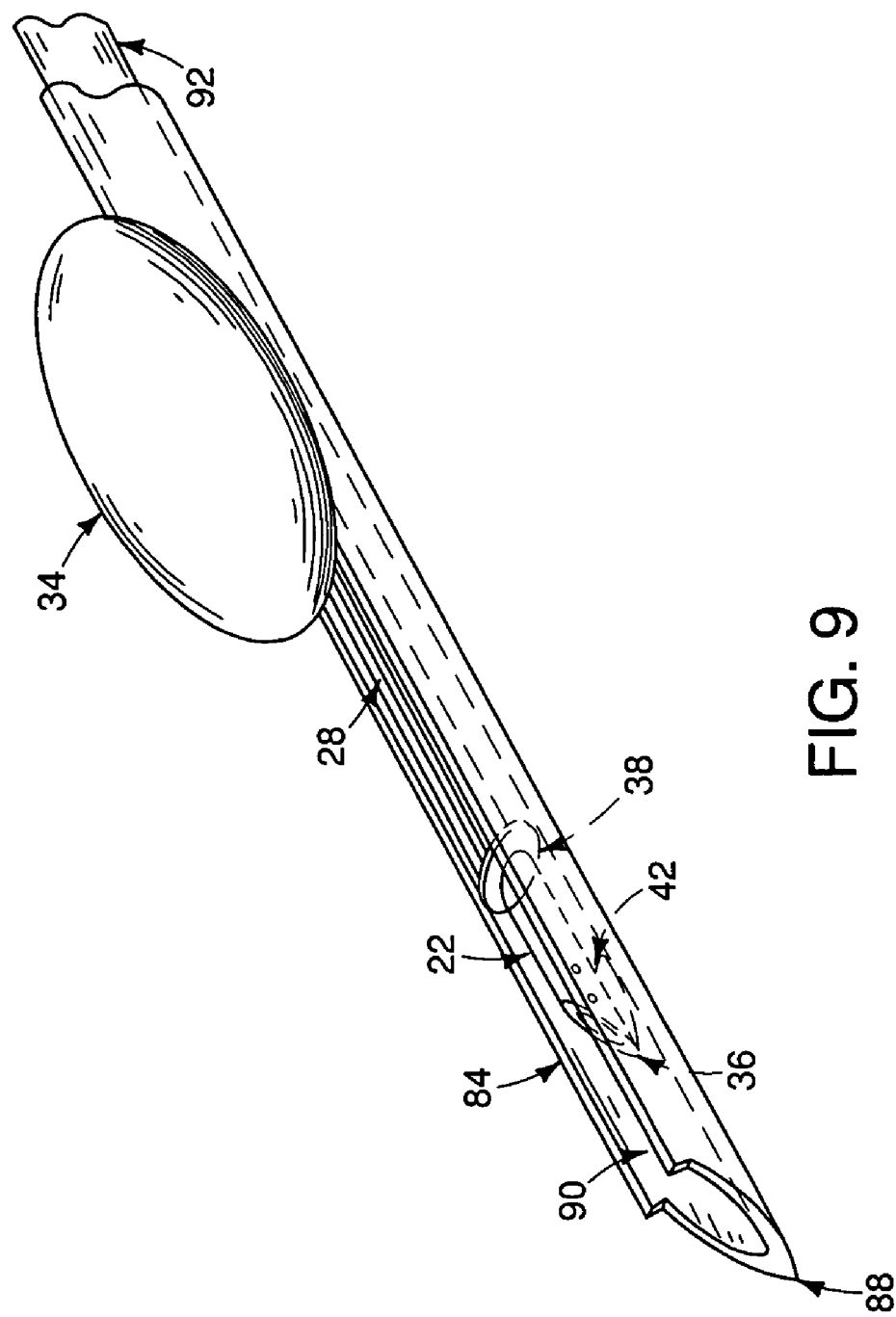
FIG. 9 is a perspective view of the drainage apparatus seated in the device to insert the drainage apparatus into an eyeball.

As shown in FIGS. 8 and 9, the inserting apparatus 82 includes an insertion prong 84 attached to a first handle 86. The insertion prong 84 has an insertion point 88. The insertion prong 84 also defines an aperture 90 wherein a second prong 92 is slideably received. As shown in FIG. 9, both the insertion prong 84 and the second prong 92 have an opening formed in their upper surface allowing for drainage apparatus 20 or 68 to be received and seated prior to insertion into the eyeball 64. The second prong 92 is attached to a second handle 94 by means of a first hinge 96. The second handle 94 is attached to the first handle 86 by means of a second hinge 98. When the first handle 86 is held in place, the second handle 94 is pushed towards the first handle 86, causing a rotation at the second hinge 98 such that the second handle 94 will push the second prong 92 toward the insertion point 88.

Figure 10:
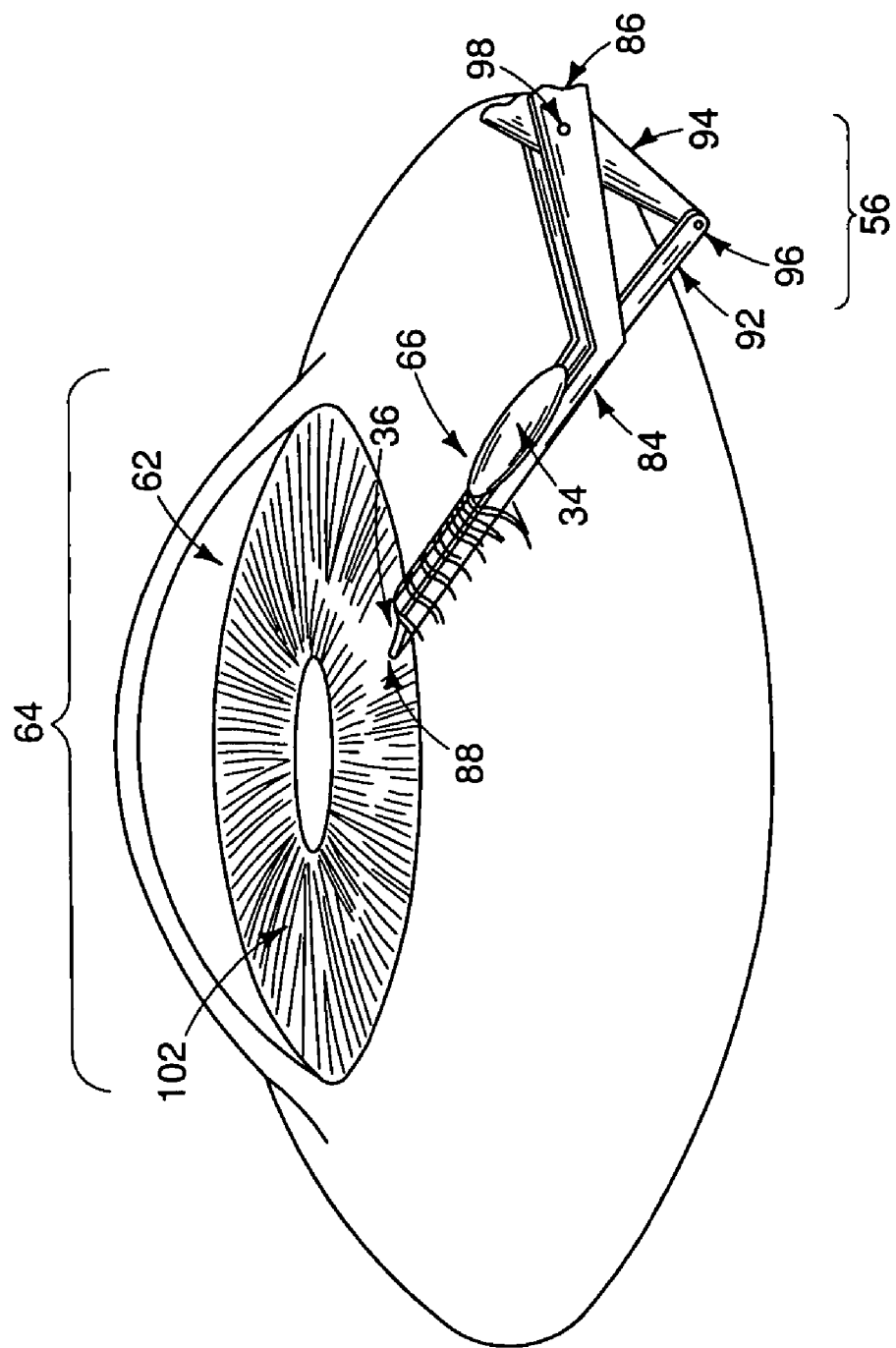
FIG. 10 is a perspective view of a device for inserting a drainage apparatus into an eyeball, a drainage apparatus, and an eyeball at the point of insertion into the eyeball.
Figure 14:
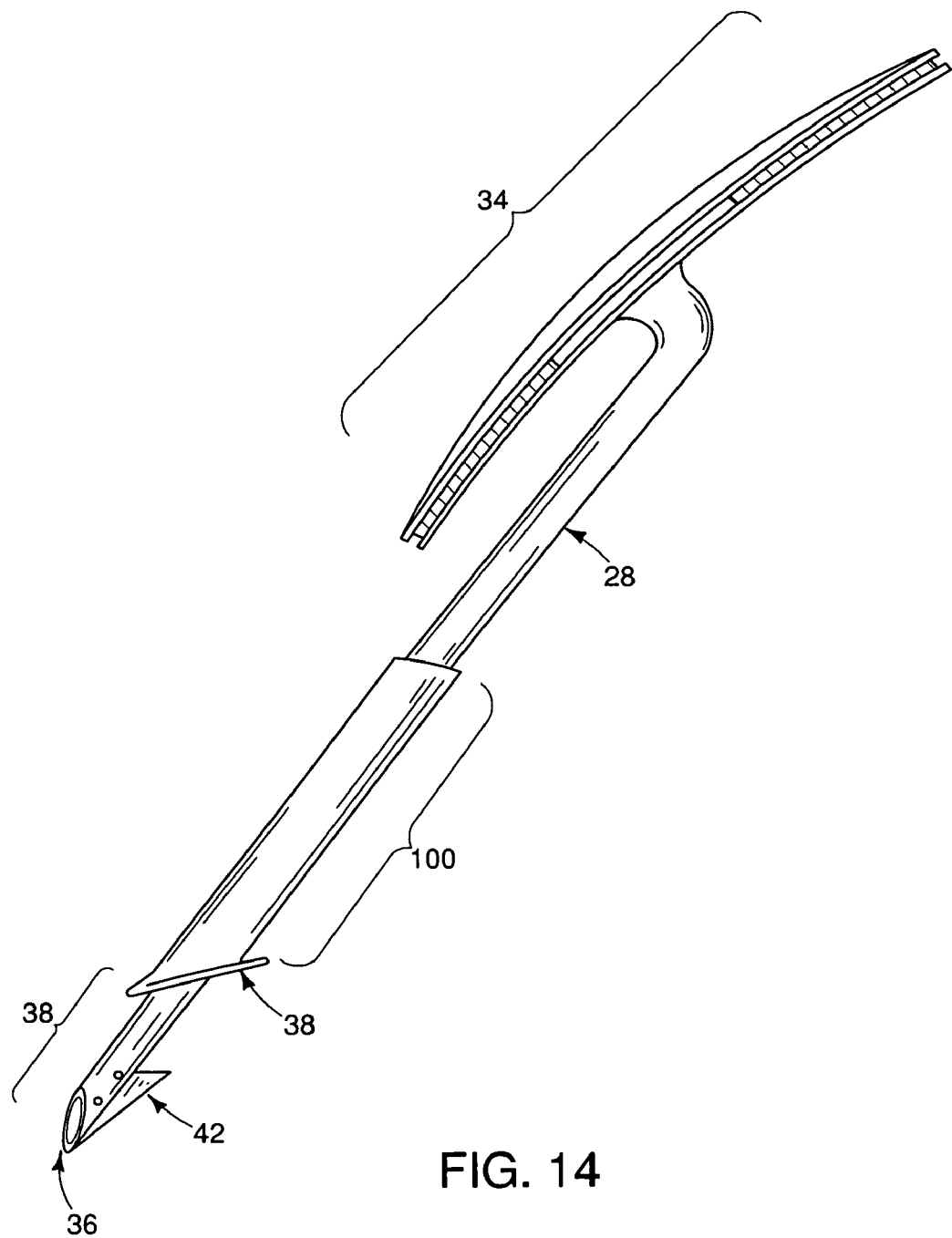
FIG. 14 is a perspective view of the drainage apparatus with a pericardial patch secured to the tube and insertion plate of the apparatus.

The process of inserting drainage apparatus 20 or 68 into the eyeball 64 with the inserting apparatus 82 is illustrated in FIG. 10. As shown in FIG. 14, a pericardial patch 100 is secured via suturing, tissue adhesive (glue) or other commonly known means around the tube 28 and insertion plate 38 of drainage apparatus 20 or 68. In addition to pericardium, patches may be fashioned of sclera, dura mater, fascia lata, or similar material. Drainage apparatus 20 or 68 is then seated within the inserting apparatus 82 such that the beveled tip 36 of the inlet assembly 22 is oriented towards the insertion point 88 of the insertion prong 84. As shown in FIG. 9, the outlet assembly 34 or one-piece outlet assembly 70 is seated along the upper external aspect of the insertion prong 84. The distal end of the second prong 92 is positioned adjacent to the anterior aspect of the insertion plate 38. FIG. 10 illustrates the position of the inserting apparatus 82 and drainage apparatus 20 or 68 at insertion into the eyeball 64, the eyeball having an iris 102, an anterior chamber 62, a conjunctival layer 66 and a limbus 104. An incision is initially made in the conjunctival layer 66. The insertion point 88 of the insertion prong 84 and the second prong 92 are guided through this incision and pushed beneath the conjunctival layer 66 to the point at which the insertion point 88 and the beveled tip 36 of the inlet assembly 22 reaches the external boundary of the limbus 104. The insertion point 88 of the insertion prong 84 may also be driven through the conjunctival layer 66 without an initial incision. In some eyeballs 64 with scarring between the conjunctival layer 66 and the underlying episcleral surface, blunt-tipped scissors can be inserted through the conjunctival incision to bluntly spread tissues to form a space between the conjunctival layer 66 and the episcleral surface. Alternatively, fluid (such a balanced salt solution) or a viscoelastic substance can be injected into this space to separate the conjunctival layer 66 from the episcleral surface. When properly aligned at limbus 104 with the insertion prong 84 and the second prong 92 positioned parallel to the plane of the iris by raising the end of the insertion device opposite the insertion point 88, the insertion point 88 is driven through the limbal tissue into the anterior chamber 62. Prior to driving insertion point 88 into the anterior chamber 62, viscoelastic material, if needed, can be injected into the anterior chamber through a separate stab incision through the peripheral cornea. After the insertion point 88 enters the anterior chamber 62, the second handle 94 is drawn towards the first handle 86, causing the second prong 92 to push against the anterior aspect of the insertion plate 38 and drive the beveled tip 36 of the inlet assembly 22 through the limbus 104 into the anterior chamber. The opening 40 of the inlet assembly 22 may then be secured in place within the anterior chamber 62 by the anchor 42, which rests against the angle or corneal endothelium in the anterior chamber 62. In addition, the insertion plate 38 rests against the external surface of the limbus 104 and also functions to hold the inlet assembly 22 in proper position. As illustrated in FIGS. 17, 18 and 20, a plurality of the anchor flanges 65 may also be formed upon the inlet assembly 22 to accommodate varying limbal thicknesses. Alternatively, the distance between anchor 42 and insertion plate 38 can be varied allowing the surgeon to choose the appropriate inlet assembly 22 according to the limbal thickness.

Figure 12:
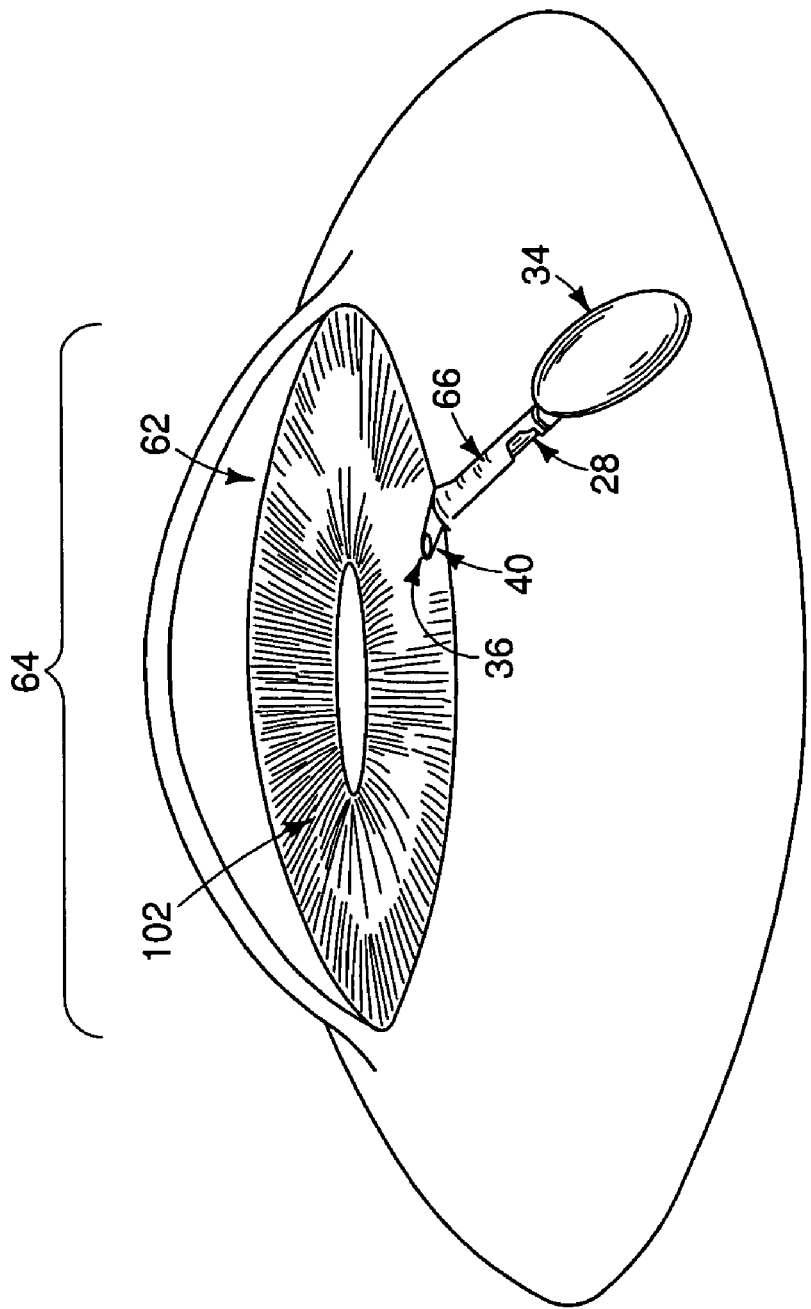
FIG. 12 is a perspective view of an eyeball into which a drainage apparatus has been inserted.

Once the inlet assembly 22 has been properly positioned, the inserting apparatus 82 is removed, leaving the drainage apparatus 20 or 68 in place as shown in FIG. 12. As illustrated in FIG. 12, once in position, the tube 28 lies comfortably on the episcleral surface, and conforms to the curvature of the eyeball 64. In this position, the conjunctival layer 66 covers the pericardial patch 100 and tube 28. The pericardial patch 100 attached to the tube 28 serves to protect the conjunctival layer 66 from eventual erosion caused by the tube 28 or the insertion plate 38. As shown in both FIG. 12 and FIG. 5, the outlet assembly 34 is ideally situated along the external ocular surface of the eyeball 64 in the conjunctival cul-de-sac, between the eyeball 64 and the upper eyelid 106 or lower eyelid 108. When inserted in this fashion, aqueous humor is directed from the anterior chamber 62 of the eyeball 64 to the tear film surface of the eyeball.

If it is necessary to secure and stabilize the outlet assembly 34 or the one-piece outlet assembly 70, a suture can be used to fix it to the underlying conjunctival layer 66. This suture can be passed through the periphery of the outlet assembly 34 or the one-piece outlet assembly 70 and through the conjunctival layer 66 only, or through both the conjunctival layer and episcleral tissue. Alternatively, fixation of the outlet assembly 34 or the one-piece outlet assembly 70 can be accomplished with tissue glue. Another means of fixation would be to coat the posterior aspect of the inner member 46 of the outlet assembly 34 or the posterior aspect of the second member 74 of the one-piece outlet assembly 70 with hydroxyapatite or similar material. If the epithelium of the conjunctival layer 66 underlying the outlet assembly 34 or the one-piece outlet assembly 70 is abraded, the conjunctiva will adhere to the hydroxyapatite on the posterior aspect of either the inner member 46 or the second member 74.

Figure 15:
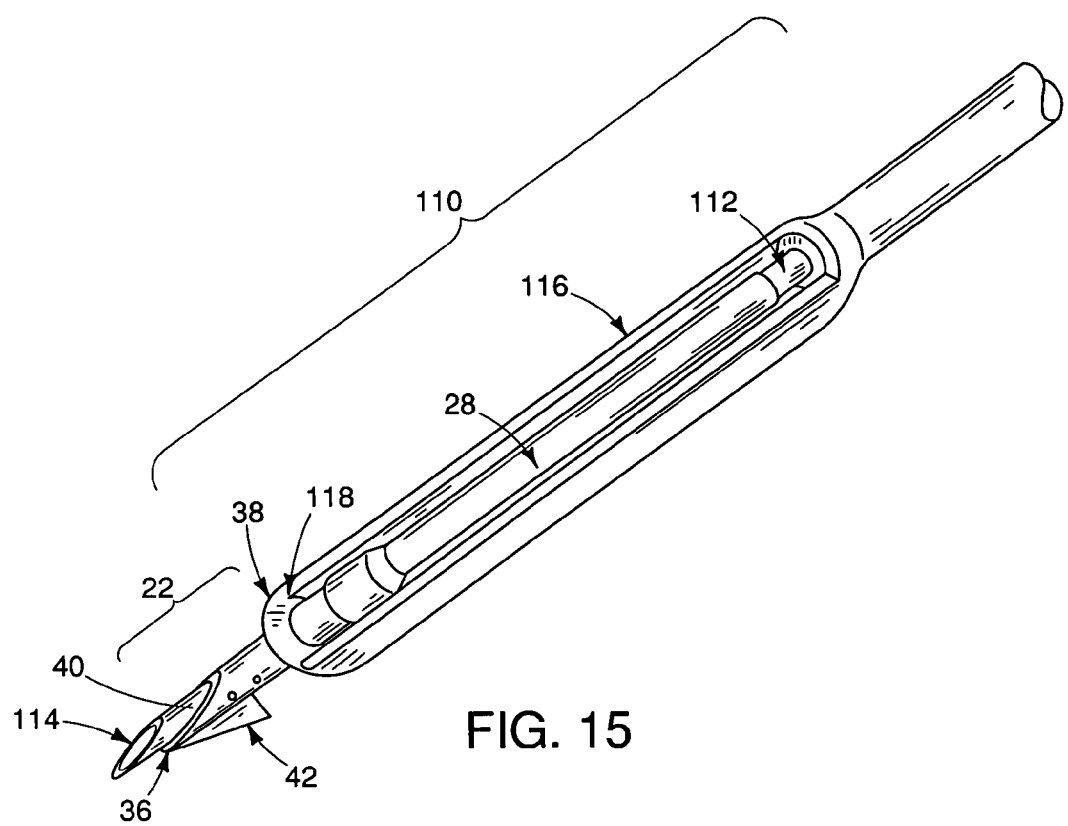
FIG. 15 is a perspective view of an alternative embodiment of a device for inserting a drainage apparatus into an eyeball, parts broken away to reveal details of construction and operation.
Figure 16:
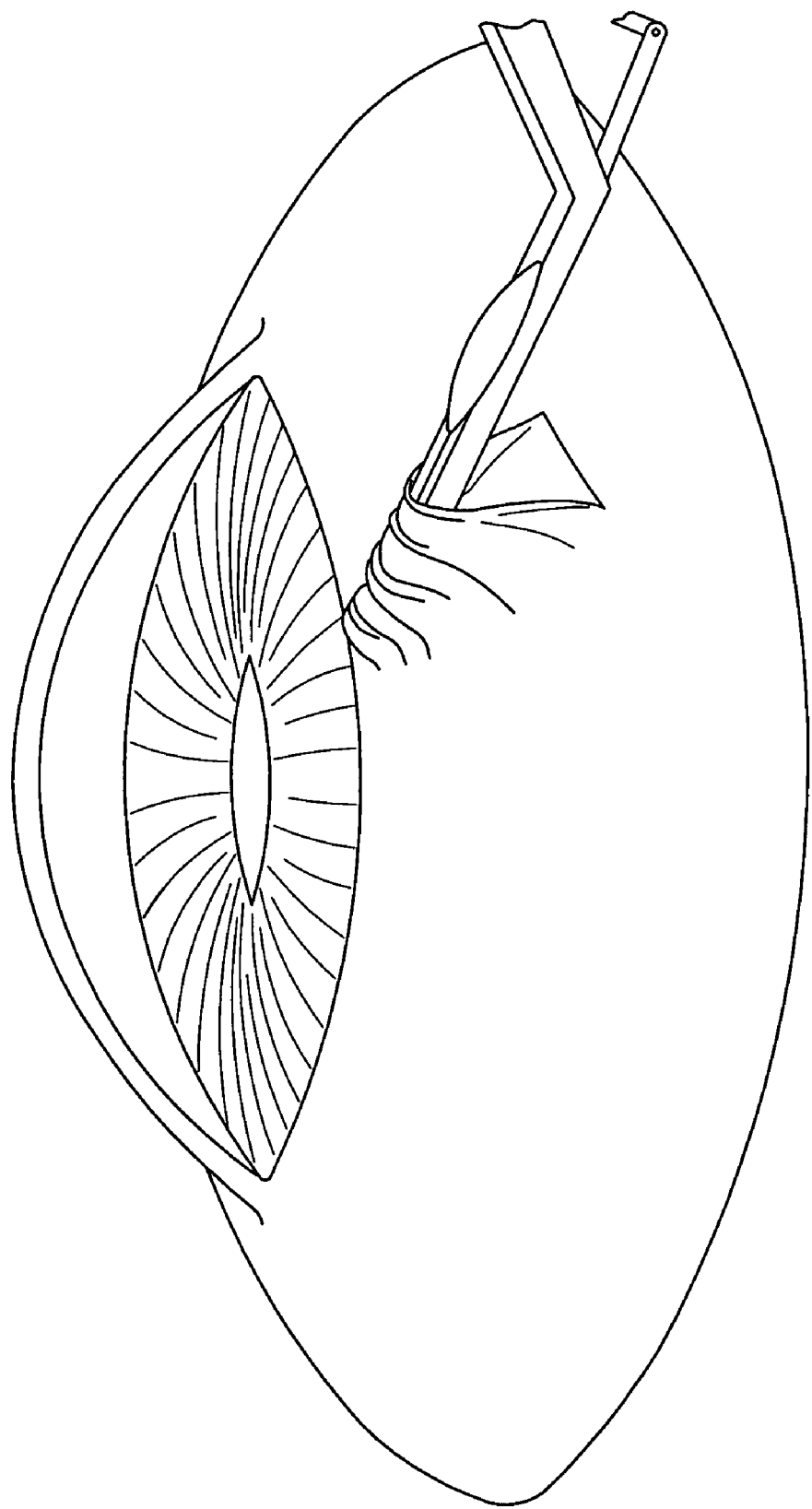
FIG. 16 is a perspective view of the device illustrated in FIG. 8 coupled to a drainage apparatus at a point of insertion into an eyeball at a preferred angle of insertion.

Another embodiment of the inserting apparatus 110 is illustrated in FIG. 15. The inserting apparatus 110 is designed to be used specifically for insertion of drainage apparatus 68. This embodiment is used to insert the inlet apparatus 22 and tube 28 of drainage apparatus 68 into the eyeball 64, allowing the one-piece outlet assembly 70 to be attached to the second end 32 of the tube 28 after insertion.

As shown in FIG. 15, the inserting apparatus 110 includes a trocar 112 having an incision end 114 and secured within an outer cylinder 116 at its opposite end. The outer diameter of the trocar 112 is slightly smaller than the inner diameter of the tube 28. The outer cylinder 116 has an open end 118 beyond which the incision end 114 of the trocar 112 extends. The outer cylinder 116 has an inner diameter slightly larger than the outer diameter of the tube 28. A pericardial patch 100 is secured around the tube 28 and the insertion plate 38 as described earlier. The tube 28 and inlet assembly 22 are then inserted over the trocar 112 within the outer cylinder 116 by inserting the incision end 114 through the second end 32 of the tube so that the incision end passes through the tube and protrudes slightly beyond the opening 40 of the inlet assembly. In this position, the incision end 114 is situated in line with the beveled tip 36 of the inlet assembly 22 and the inlet assembly protrudes beyond the distal end of the outer cylinder 116 but still surrounds the incision end of the trocar 112. The insertion plate 38 is positioned against the open end 118 of the outer cylinder 116.

An incision is first made in the conjunctival layer 66 with either a scissors or with the incision end 114 of the trocar 112, and the inlet assembly 22, tube 28, outer cylinder 116 and trocar are then guided through this incision and pushed beneath the conjunctival layer 66 to the point at which the incision end of the trocar reaches the external boundary of the limbus 104. In certain eyeballs, the conjunctival layer 66 may need to be separated from the underlying episcleral tissue with blunt dissection, fluid, or viscoelastic material as previously described. At this point, the outer cylinder 116 and trocar 112 are pushed forward with an orientation parallel to the plane of the iris, causing the incision end 114 of the trocar to pierce through the limbus 104. This also causes the outer cylinder 116 to press against the insertion plate 38 and drive the beveled tip 36 of the inlet assembly 22 through the limbus 104 into the anterior chamber 62. The opening 40 of the inlet assembly 22 may then be secured in place within the anterior chamber 62 as previously described. The outer cylinder 116 and trocar 112 are then removed, and the tube 28 remains in position subconjunctivally as previously described.

The second end 32 of the tube 28 exits through the initial incision of the conjunctival layer 66 several millimeters posterior from the limbus 104. The one-piece outlet assembly 70 is then attached to the second end 32 of the tube 28 by attaching a plunger or similar suctioning device 120 to the external surface of the first member 72. The coupling mechanism 78 of the one-piece outlet assembly 70 is then guided into position over the second end 32 of the tube 28. Once in place, manual pressure is applied to seat the coupling mechanism 78 into the second end 32 of the tube 28. The one-piece outlet assembly 70 lies in the same position as the outlet assembly 34 in FIGS. 5 and 12, along the external ocular surface of the eyeball 64 in the conjunctival cul-de-sac between the eyeball and the upper eyelid 106 or lower eyelid 108. When inserted in this fashion, aqueous humor is directed from the anterior chamber 62 of the eyeball 64 to the tear film surface of the eyeball.

Figure 7:
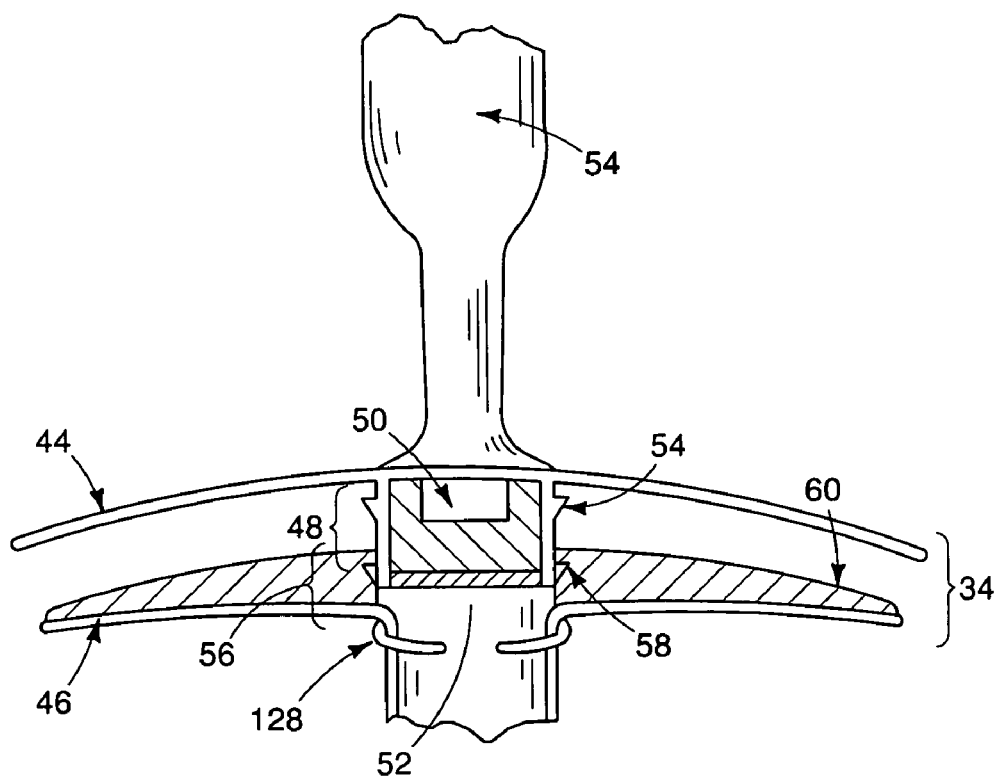
FIG. 7 is a cross-sectional view of the outlet assembly of the drainage apparatus shown in FIGS. 1-4 with a suctioning device attached to the outer member and inserting it upon the inner member.
Figure 13:
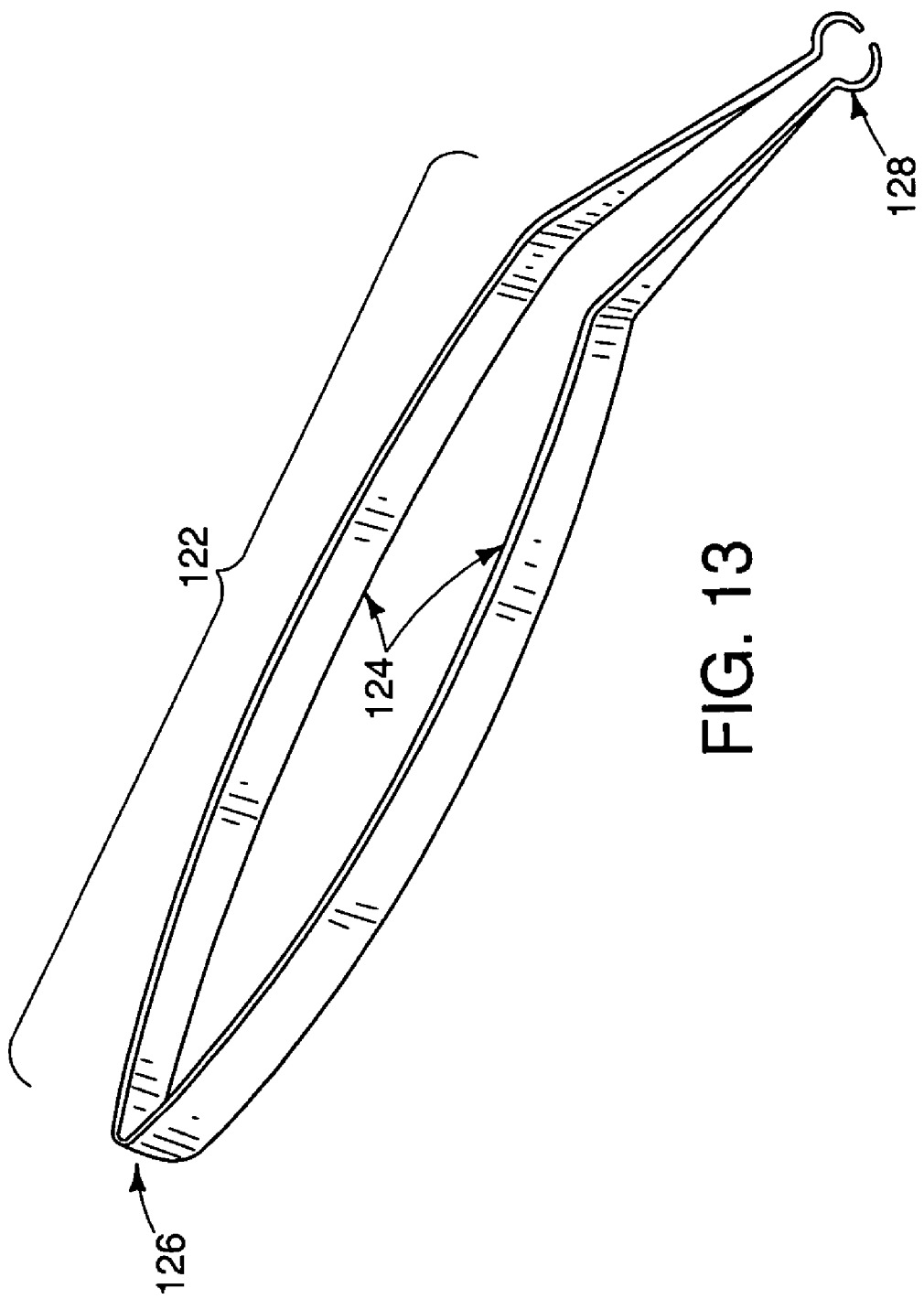
FIG. 13 is a perspective view of a device for stabilizing a drainage apparatus to allow for the removal and replacement of valves or filters within the drainage apparatus.

The present invention also provides for removal and replacement of the filter 52 and/or valve 80 from drainage apparatus 20 or 68. This feature allows for the rate of outflow of aqueous humor from the anterior chamber 62 of the eyeball 64 through drainage apparatus 20 or 68 to be post-surgically adjusted in a predictable manner. In drainage apparatus 20, this process involves removing and replacing the outer member 44 which houses the filter 52 and/or valve 80 in the central chamber 48. In order to remove and replace the outer member 44 and filter 52, the outlet assembly 34 must first be stabilized. This is accomplished by use of the grasping apparatus 122 illustrated in FIG. 13. The grasping apparatus 122 includes two elongated members 124, joined at their proximal end 126, which taper to form an opposable grasping structure 128 at their distal end. This opposable grasping structure 128 is shaped to match the external contour of the second end 32 of the tube 28, thereby allowing a user to grasp the second end of the tube so as to secure the outlet assembly 34 as illustrated in FIG. 7. Once the outlet assembly 34 is secured, the outer member 44 may be removed from the inner member 46 by cutting the superficial aspect of the central chamber 48 of the outer member with a scalpel or other surgical cutting tool and removing it from the inner member with a forceps. The flange 54 must also be removed from the groove 58 of the central cavity 56. The design of drainage apparatus 20 allows for the outer member 44 to be easily removed in this manner without damaging the inner member 46. Once the outer member 44 is removed, a new outer member and filter 52 can be attached to the inner member 46. As illustrated in FIG. 7, a plunger or similar suctioning device 120 is attached to the external surface of a replacement for the outer member 44, which allows the outer member to be guided into place by aligning the central chamber 48 of the outer member into the central cavity 56 of the inner member 46. Once in place, manual pressure is applied to seat the flange 54 of the central chamber 48 within the groove 58 of the central cavity 56. Once this attachment is made, the plunger or similar suctioning device 120 is removed from the outer member 44, leaving the outer member in place. Alternate methods for removing and replacing the outer member 44 from the outlet assembly 34 may also be used.

Removal and replacement of the filter 52 and/or valve 80 in drainage apparatus 68 is accomplished through the removal and replacement of the one-piece outlet assembly 70. The grasping apparatus 122 is used to grasp the second end 32 of the tube 28. Once the second end 32 of the tube 28 is secured, the one-piece outlet assembly 70 may be removed by sectioning it centrally with a scalpel or other surgical cutting device. A forceps may be used to grasp the one-piece outlet assembly 70 either centrally or more peripherally as necessary to help facilitate this process. The method for inserting a replacement one-piece outlet assembly 70 is similar to the procedure described above. A plunger or similar suctioning device 120 is attached to the external surface of the first member 72 of a replacement for the one-piece outlet assembly 70, and the coupling mechanism 78 of the one-piece outlet assembly 70 is guided into position over the second end 32 of the tube 28. Once in place, manual pressure is applied so as to seat coupling mechanism 78 into the second end 32 of the tube 28. The plunger or similar suctioning device 120 is then removed. Alternate methods for removing and replacing the one-piece outlet assembly 70 from drainage apparatus 68 may also be employed.

The method to change filters in drainage apparatus 20 and 68 disclosed herein as a means to predictably control and regulate the level of intraocular pressure in the eyeball 64 without invasive surgery is a novel feature of the present invention. This feature allows one to predictably control the flow of aqueous humor out of the anterior chamber 62 of the eyeball 64 to achieve a predetermined postoperative target intraocular pressure. If the postoperative intraocular pressure is unacceptably high or low, the current filter 52 with or without valve 80 can be replaced with a filter 52 with or without valve 80 to increase or decrease the flow of aqueous humor out of the eyeball 64, thus reducing or increasing the intraocular pressure in the eyeball.

The outlet assembly 34 of drainage apparatus 20 is designed so that the implant site, the central cavity 56 and the filter 52 and/or valve 80 are surrounded by the outer member 44 and inner member 46, and are not directly exposed to the external surface of the eyeball 64. The same is true with drainage apparatus 68, wherein the first member 72 and second member 74 surround the implant site and the filter 52 and/or valve 80. This feature of drainage apparatus 20 and 68 greatly reduces the possibility of foreign material entering and clogging drainage apparatus 20 or 68, subsequently hindering or negating its function. In addition, a filter 52 with appropriate pore diameter presents an absolute barrier against bacterial infiltration of drainage apparatus 20 or 68, preventing the possibility of an intraocular infection. The present invention may also incorporate a layer of hydroxyapatite or similar material around the second end 32 of the tube 28 to stimulate the growth of the surrounding conjunctival layer 66 into the external surface of the tube, thereby providing a barrier around the external aspect of drainage apparatus 20 or 68.

The use of drainage apparatus 20 and 68, and inserting apparatus 82 and 110 provide tremendous advantages over the prior art. Other drainage devices and surgical techniques designed to decrease intraocular pressure and treat glaucoma are invasive and lengthy procedures, requiring multiple incisions into the eyeball. Patients often face long postoperative recovery periods following such procedures. Other drainage devices in the art are also very difficult to properly insert, and operate to drain aqueous humor into a bleb or fibrous capsule which can scar and cease to function over time requiring additional surgery to correct. Inserting apparatus 82 and 110 provide a greatly simplified procedure for insertion of drainage apparatus 20 and 68, requiring only one incision in the conjunctival layer 66, and in certain instances no incisions at all. Drainage apparatus 20 or 68 also drains aqueous humor out of the eyeball entirely, negating the need for the creation of either a fibrous capsule or a bleb. Since the insertion procedure for the present invention is greatly simplified, the operating and recovery time for the patient is considerably shortened. The insertion procedure for the present invention is far less invasive than other surgical procedures currently used to increase aqueous humor drainage or insert drainage devices. A significant advantage of the present invention compared to commercially available devices is that the outcome of the surgical procedure is reliably predictable because it is independent of the vagaries of wound healing. The possibilities of insufficient wound healing leading to hypotony, and excessive healing resulting in failure are eliminated. In addition, the convex lens shape of the outlet assembly 34 and one-piece outlet end 70 makes the use of drainage apparatus 20 or 68 comfortable for the patient.

Optimally, the inlet assembly 22 of the drainage apparatus 20 and 68 is formed from Silastic® material. Alternatively, a hard plastic, such as polymethyl methacrylate (PMMA), a durable glass or surgical metal, such as surgical steel, may be required. The material from which the inlet assembly 22 is composed may need to be resilient to facilitate the insertion procedure. A hard, resilient material would enable the inclusion of optional inlet holes 130 distal to the opening 40 in the event that the opening 40 becomes occluded with intraocular tissue. Such holes 130 would also reduce the possibility of the opening 40 becoming occluded during the use of drainage apparatus 20 or 68. However, the design of the insertion point 88 of inserting apparatus 82 is sufficient to pierce the limbus 104 so as to allow the inlet assembly 22 to be properly positioned within the anterior chamber 62, without necessarily requiring a hard material for the inlet assembly. Likewise, the incision end 114 of the trocar 112 of inserting apparatus 110 may negate the need for a hard material for the inlet assembly 22. A softer material for the inlet assembly 22 would reduce the possibility of damage to intraocular tissues such as the cornea, iris or lens.

The tube 28 is optimally formed from a highly durable yet flexible material, such as Silastic® or silicone. The tube 28 must be flexible, but should not be easily ruptured, bent or kinked so as to stop the flow of aqueous humor or hinder the drainage function of the drainage apparatus 20 or 68. The external surface of the tube 28, particularly the area nearest the outlet assembly 34 or 70, is optimally coated with a material such as hydroxyapatite so as to enable the growth of the surrounding conjunctival layer 66 into the external surface of the tube 28, providing an absolute barrier between the outside surface of the tube and the conjunctival layer surrounding the tube on the outer surface of the eyeball 64. The filter 52 may be formed from polycarbonate, although many other materials would also be suitable. And as discussed earlier, valves 80 for use in the drainage apparatus 20 or 68 may be formed from silicone or Silastic® material.

Other suitable filter types, valves and materials for the tube 28, inlet assembly 22, outlet assembly 34, and one-piece outlet assembly 70 of drainage apparatus 20 or 68 may be used in accordance with the present invention and will be apparent to those of skill in the art.

FIGS. 21a and 21b illustrate an alternative preferred embodiment for a valve and filter assembly, indicated generally at 132. A valve 134 includes a central chamber 136 with a drainage aperture 138 disposed therein. A filter 140 extends across an underside of the valve 134 to enclose a generally U-shaped space. An elastic member 142 having an elastic opening 144 therethrough is disposed within the U-shaped space. When there is insufficient pressure to stretch the elastic member 142, the elastic member remains in a relaxed state, and there is no flow through the drainage aperture 138, as illustrated in FIG. 21a. However, when sufficient fluid pressure is exerted on the filter 140, the elastic member 142 will stretch, opening the elastic opening 144, and exerting upward pressure on the valve 134 until the elastic opening at least partially overlaps the drainage aperture 138. In this manner, as illustrated in FIG. 21b, the valve and filter assembly 132 promote outflow of aqueous humor at sufficient pressure.

Figure 22:
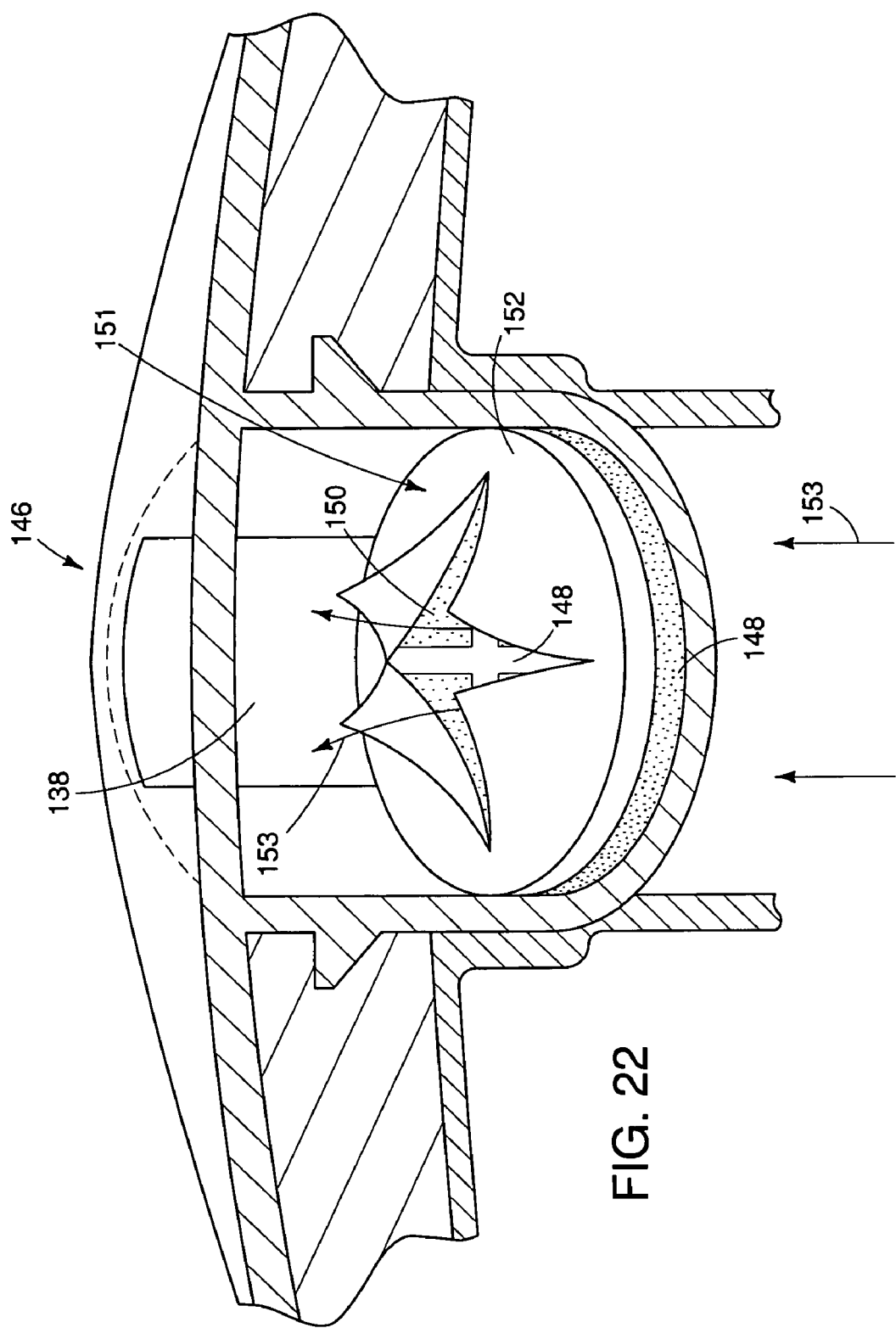
FIG. 22 is cross-sectional view of an outlet assembly with a top perspective view of a filter and valve where the filter is perforated to permit flow therethrough at sufficient fluid pressure.

FIG. 22 illustrates still another alternative preferred embodiment for a valve and filter assembly, generally at 146. A filter 148 having areas 150 of perforations is disposed at an underside of a valve, indicated generally at 151, having four flexible flap portions 152 that are configured to open upwardly in a direction opposite the filter 148. The filter 148 provides a physical barrier to movement of the flap portions downwardly as shown, thereby restricting movement of aqueous to a unidirectional flow as shown by arrows 153. The configuration of the valve 151 may comprise a greater or lesser number of flap portions and the area and size of the perforations in the filter 148 can be varied to control the flow of aqueous humor through the valve and filter assembly and therefore through the drainage aperture 138.

Figure 23:
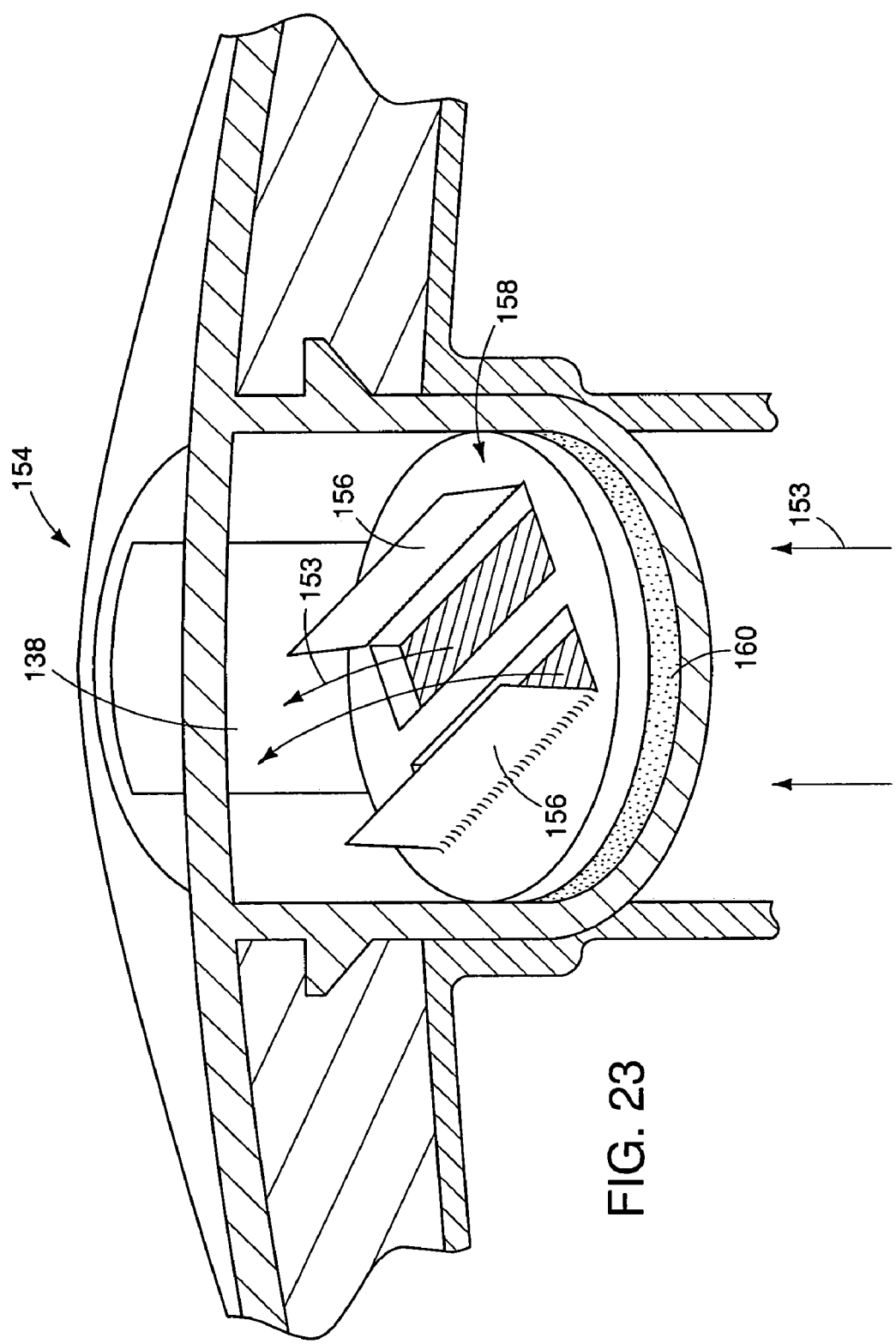
FIG. 23 is an alternative preferred embodiment of the filter of FIG. 22.

FIG. 23 illustrates yet another alternative preferred embodiment for a valve and filter assembly, generally at 154. One or more doors 156 are disposed on a top surface of a valve 158. A filter 160 disposed at an underside of the valve 158 ensures unidirectional opening of the doors 156 under sufficient fluid pressure to permit flow of aqueous humor through the doors 156 and subsequently through the drainage aperture 138.

Use of the present invention as a means to treat glaucoma will allow for maintenance of a predictable post-surgical intraocular pressure which can be further modified as necessary to achieve a desired result. The present invention is comfortable and durable, and reduces the possibility of further damage to the optic nerve and visual loss resulting from excessively high or low intraocular pressure. The present invention also lessens the need for additional treatments or surgical procedures and their inherent risks, procedures which may result in further damage to vision. The insertion procedure for the present invention is far less invasive than other surgical procedures, including the procedures for inserting other drainage devices currently used to increase aqueous humor drainage. In addition, the present invention limits the risk of infection for the patient by providing an absolute barrier against infection compared with the cystic, thin-walled blebs that often occur with standard filtration procedures performed in conjunction with anti-scarring agents such as mitomycin C or 5-fluorouracil.

Various features of the invention are set forth in the following claims.

What is claimed is:

1. A drainage apparatus to reduce intraocular pressure in an eyeball that includes an anterior chamber having aqueous humor disposed therein, a cornea and a surrounding marginal limbus by which the cornea is continuous with a scleral layer and a conjunctival layer disposed on an exposed surface of the eyeball and under eyelids, said apparatus comprising:
   an inlet assembly configured to be disposed at the anterior chamber of the eyeball;
   an outlet assembly configured to be disposed at the external surface of the eyeball, said outlet assembly comprising inner and outer convex members;
   said inner and outer convex members being separated, thereby providing openings to allow aqueous humor to exit around the outer periphery thereof onto the external ocular surface, said inner and outer convex members being configured to generally correspond to the external surface of the eyeball, said inner member having a central cavity disposed therein and said outer member having a central chamber and at least one aperture disposed therein, where said central cavity and said central chamber are configured to matingly engage one another;
   a tube extending between said inlet and outlet assemblies and configured to promote fluid communication between said inlet and outlet assemblies; and
   control structure disposed within said outlet assembly for controlling a flow of aqueous humor through said tube from said anterior chamber of the eyeball to said external surface of the eyeball, and for preventing bacterial infiltration into the anterior chamber, said control structure comprising a replaceable filter disposed within said central chamber of said outer convex member, said outer convex member being configured to be removeable to facilitate removal and replacement of said filter without removing said inner convex member.

2. The apparatus of claim 1, said inlet assembly comprising first and second inlet assembly ends and an anchor structure for securing said inlet assembly within the anterior chamber of the eyeball.

3. The apparatus of claim 2, said anchor structure comprising a flange configured to engage a corneal endothelium of the eyeball.

4. The apparatus of claim 2, said anchor structure comprising a plurality of flanges adjacent one another along the length of said anchor structure configured to selectively engage the corneal endothelium of the eyeball at varying depths to accommodate varying limbal thicknesses.

5. The apparatus of claim 2, said anchor structure further comprising an insertion plate configured to abut an external surface of the limbus for securing said inlet assembly to the eyeball.

6. The apparatus of claim 5 further comprising a patch fixedly secured to said tube by a fixative prior to implantation to prevent extrusion of and erosion of the conjunctival layer of the eye near said apparatus after implantation.

7. The apparatus of claim 6 wherein said patch comprises a pericardial patch.

8. The apparatus of claim 6, said fixative comprising either sutures or an adhesive material.

9. The apparatus of claim 8 wherein said adhesive material comprises glue.

10. The apparatus of claim 1, said replaceable filter comprising polycarbonate.

11. The apparatus of claim 1 wherein a porosity of said filter is configured to selectively optimize a flow of aqueous humor.

12. The apparatus of claim 1, said control structure comprising a pressure-sensitive valve for providing a predetermined amount of resistance to control a flow of aqueous humor into said outlet.

13. The apparatus of claim 1 further comprising a replaceable valve disposed between said replaceable filter and said at least one aperture of said central chamber.

14. The apparatus of claim 1 further comprising at least one layer of growth-stimulating material disposed substantially around an outer circumference of said tube to promote ingrowth of the conjunctival layer and to provide a barrier to prevent bacterial migration in a vicinity of said tube.

15. The apparatus of claim 14 wherein said layer of growth-stimulating material comprises hydroxyapatite.

16. The apparatus of claim 1, said at least one convex member being configured to be unitary and removable as a single piece.

17. The apparatus as defined in claim 1, further comprising a plurality of spacers located between said inner and outer members to enable aqueous humor to flow from said central chamber to the outer periphery of said inner member, said outlet assembly having a plurality of openings distributed around the outer periphery thereof through which aqueous humor can exit to the external surface of the eyeball.

18. The apparatus of claim 17 wherein said spacers are formed with said inner member and are pie shaped with adjacent spacers being spaced apart from one another to define said flow paths.

19. The apparatus of claim 17 wherein one of said inner and outer members have said plurality of openings.

20. The apparatus of claim 17 wherein said plurality of openings comprise a plurality of elongated slots.

21. A drainage apparatus to reduce intraocular pressure within an eyeball, the eyeball having aqueous humor, a curved external surface having multiple points of ingress disposed thereon, and an anterior chamber, a conjunctival layer and a limbus, said apparatus comprising:
   an inlet assembly disposed within the anterior chamber for ingress of aqueous humor from the anterior chamber;
   an outlet assembly disposed externally to the eyeball for draining aqueous humor exterior to the eyeball, said outlet assembly comprising inner and outer convex members with a central chamber located in one of said inner and outer convex members, said inner and outer convex members having a space between them, thereby providing openings to allow aqueous humor to exit around the outer periphery thereof onto the external ocular surface, said members being configured to matingly engage one another, said outer convex member being removable from said inner convex member, and said inner convex member abutting the external surface of the eyeball;
   a conduit for conducting a flow of aqueous humor between said inlet assembly and outlet assembly;
   control structure for controlling the flow of aqueous humor between said inlet assembly and outlet assembly, said control structure disposed within said central chamber and comprising a replaceable filter and a replaceable valve; and
   an anchor structure for preventing extrusion of said apparatus.

22. The apparatus of claim 21, said inlet assembly comprising an elongated body having an axial orifice therethrough.

23. The apparatus of claim 22, said inlet assembly having a beveled end configured pierce the anterior chamber.

24. The apparatus of claim 23, said anchor structure comprising at least one generally triangular flange extending outwardly at the beveled end of said inlet assembly.

25. The apparatus of claim 24, said anchor structure further comprising a radial insertion plate disposed at an end of said inlet assembly opposite said beveled end.

26. The apparatus of claim 25, said radial insertion plate configured to abut an external surface of a limbus for securing said inlet assembly to the eyeball.

27. The apparatus of claim 23, said anchor structure comprising a plurality of axial flanges extending outwardly at the beveled end of said inlet assembly.

* * * * *